United States Patent
Jaquish et al.

(10) Patent No.: US 9,084,912 B2
(45) Date of Patent: *Jul. 21, 2015

(54) SYSTEMS AND METHODS FOR ADMINISTERING AN EXERCISE PROGRAM

(75) Inventors: John Paul Jaquish, Nevada City, CA (US); Paul Edward Jaquish, Nevada City, CA (US)

(73) Assignee: Performance Health Systems, LLC, Nevada City, CA (US)

(*) Notice: Subject to any disclaimer, the term of this patent is extended or adjusted under 35 U.S.C. 154(b) by 986 days.

This patent is subject to a terminal disclaimer.

(21) Appl. No.: 13/091,002

(22) Filed: Apr. 20, 2011

(65) Prior Publication Data
US 2012/0040799 A1 Feb. 16, 2012

Related U.S. Application Data

(60) Continuation-in-part of application No. 12/887,431, filed on Sep. 21, 2010, now Pat. No. 7,959,540, which is a continuation of application No. 12/534,001, filed on Jul. 31, 2009, now Pat. No. 7,806,806, which is a division of application No. 11/254,289, filed on Oct. 19, 2005, now Pat. No. 7,753,825.

(51) Int. Cl.
*A63B 23/035* (2006.01)
*A63B 21/00* (2006.01)
(Continued)

(52) U.S. Cl.
CPC ....... *A63B 23/03558* (2013.01); *A63B 21/0023* (2013.01); *A63B 21/00047* (2013.01); *A63B 21/1469* (2013.01); *A63B 23/0355* (2013.01); *A63B 23/03525* (2013.01);
(Continued)

(58) Field of Classification Search
CPC ............... A63B 23/03558; A63B 23/03525; A63B 23/0355; A63B 21/00047; A63B 21/0023; A63B 21/1469
USPC ............ 482/1-9, 51, 900-902; 434/247-259; 73/379.01-379.03; 601/23
See application file for complete search history.

(56) References Cited

U.S. PATENT DOCUMENTS 4,466,610 A 8/1984 Israel
4,556,214 A 12/1985 Petrofsky et al.
(Continued)

FOREIGN PATENT DOCUMENTS

WO   WO 2010/059061 A1   5/2010

OTHER PUBLICATIONS

The International Bureau of WIPO, International Preliminary Report on Patentability dated Apr. 23, 2008 for International Application No. PCT/US2006/041190.

(Continued)

*Primary Examiner* — Glenn Richman
(74) *Attorney, Agent, or Firm* — Morgan, Lewis & Bockius LLP

(57) ABSTRACT

An exercise machine includes loading contact surfaces. An actuator is configured to adjust a position of the loading contact surface. A user controls the actuator through a user interface to adjust the loading contact surface's position in a first exercise session. A processor is configured to automatically monitor the loading contact surface's position as adjusted by the user in the first exercise session, and to automatically control the actuator to move the loading contact surface in a subsequent session to the same or a different position as in the previous session.

26 Claims, 21 Drawing Sheets

(51) Int. Cl.
   *A63B 21/002*   (2006.01)
   *A63B 24/00*    (2006.01)
   *G06F 19/00*    (2011.01)
   *A63B 71/00*    (2006.01)

(52) U.S. Cl.
   CPC ........ *A63B 24/0062* (2013.01); *A63B 24/0075* (2013.01); *G06F 19/3481* (2013.01); *A63B 71/0054* (2013.01); *A63B 2024/0068* (2013.01); *A63B 2208/0204* (2013.01); *A63B 2220/51* (2013.01); *A63B 2220/58* (2013.01); *A63B 2220/62* (2013.01); *A63B 2220/833* (2013.01); *A63B 2225/096* (2013.01); *A63B 2225/15* (2013.01); *A63B 2225/20* (2013.01)

(56) References Cited

U.S. PATENT DOCUMENTS

| | | | |
|---|---|---|---|
| 4,571,682 | A | 2/1986 | Silverman et al. |
| RE35,598 | E | 9/1997 | Sadoff |
| 6,159,131 | A | 12/2000 | Pfeffer |
| 6,296,595 | B1 | 10/2001 | Stark et al. |
| 6,375,598 | B1 | 4/2002 | Frame |
| 6,436,058 | B1 | 8/2002 | Krahner et al. |
| 6,515,593 | B1 | 2/2003 | Stark et al. |
| 6,561,951 | B2 | 5/2003 | Cannon |
| 6,582,342 | B2 | 6/2003 | Kaufman |
| 6,595,901 | B2 * | 7/2003 | Reinbold et al. ............ 482/91 |
| 6,643,385 | B1 | 11/2003 | Bravomalo |
| 6,746,370 | B1 | 6/2004 | Fleming |
| 7,063,644 | B2 | 6/2006 | Albert et al. |
| 7,070,539 | B2 | 7/2006 | Brown et al. |
| 7,182,719 | B2 | 2/2007 | Tuller |
| 7,371,216 | B2 * | 5/2008 | Weyand et al. ............ 600/300 |
| 7,618,347 | B2 * | 11/2009 | Yeo et al. ............ 482/8 |
| 7,666,118 | B1 * | 2/2010 | Anthony ............ 482/8 |
| 2002/0072655 | A1 | 6/2002 | Pfeffer |
| 2002/0091039 | A1 | 7/2002 | Reinhold et al. |
| 2002/0128119 | A1 | 9/2002 | Arai |
| 2003/0013071 | A1 | 1/2003 | Thomas |
| 2003/0032524 | A1 | 2/2003 | Lamar |
| 2004/0077462 | A1 | 4/2004 | Brown |
| 2004/0110602 | A1 | 6/2004 | Feldman |
| 2004/0117214 | A1 | 6/2004 | Shea |
| 2004/0127336 | A1 | 7/2004 | Lapcevic |
| 2004/0198555 | A1 | 10/2004 | Anderson et al. |
| 2005/0020415 | A1 | 1/2005 | Reno |
| 2005/0107726 | A1 | 5/2005 | Oyen |
| 2007/0027006 | A1 | 2/2007 | Suiter |
| 2008/0248926 | A1 | 10/2008 | Cole et al. |
| 2010/0234196 | A1 | 9/2010 | Shinomiya |
| 2012/0040799 | A1 | 2/2012 | Jaquish |

OTHER PUBLICATIONS

ISA/US, International Written Opinion dated Aug. 16, 2007 for International Application No. PCT/US2006/041190.

Supplementary Search Report for EP Application No. 06826421.7 dated Aug. 3, 2012.

International Search Report and Written Opinion for International Application No. PCT/US2012/34552 dated Jan. 25, 2013.

* cited by examiner

SYSTEMS AND METHODS FOR ADMINISTERING AN EXERCISE PROGRAM

CROSS-REFERENCE TO RELATED APPLICATIONS

This is a continuation-in-part of U.S. patent application Ser. No. 12/887,431, filed Sep. 21, 2010, which is a continuation of U.S. patent application Ser. No. 12/534,001, filed Jul. 31, 2009 (now U.S. Pat. No. 7,806,806), which is a division of U.S. patent application Ser. No. 11/254,289, filed Oct. 19, 2005 (now U.S. Pat. No. 7,753,825), all the above applications hereby incorporated herein by reference.

TECHNICAL FIELD

This application relates to the systems and methods used to facilitate a fully contracted exercise program for subjects interested in improving their health and fitness and further relates to the use of resistance exercise for treating certain diseases.

FIELD OF THE INVENTION

Systems and methods are provided to facilitate a fully contracted exercise program for subjects interested in improving their health and fitness.

BACKGROUND

Experts in the field of sports medicine have identified the increasing problem of exercise related injuries. G. O. Matheson, MD, Ph.D., and editor of *The Physician and Sports Medicine*, wrote "Almost two decades ago, great attention was paid to physical fitness, technique, and equipment design as protective against injury. Hopes were high that these measures would reduce injuries. Yet according to recent statistics, the incidence of injuries is at an all time high." As an example, the *U.S. Consumer Product Safety Commission*, 2001, reported a continuing and escalating increase in sports/exercise participation due to the baby boomer demographics. Not surprisingly, there has been a coincident increase in sports/exercise related injuries. This same report documents sports and exercise injuries in the age group 35 to 54 increasing about thirty-three percent between 1991 and 1998. Furthermore, recently released Frost and Sullivan Fitness Industry Statistics show the phenomenal growth of people over 55 in fitness almost suggesting an emerging branch of "geriatric sports medicine."

Existing fitness programs' lack of sustainability is also an increasing problem in the fitness industry. Less than five percent of the United States population consistently maintains strength and fitness throughout their adult life. A multitude of fitness programs and centers have been developed and literally countless fitness products have been promoted over the past 30 years, but many of these programs have largely been unsatisfactory. *Fitness Management Magazine*, 2005 published Frost & Sullivan data stating that the average home exercise equipment is used for only one year, and the average fitness center membership lasts only two years. These disappointing statistics support the argument that the fitness industry needs a new solution with safety, longevity and sustainability as its primary goal.

Moreover, almost without exception the fitness industry has underestimated the importance of allowing time for tissue recovery. As a result, the potential benefits of exercise participation are often reduced and the chances of injury are increased. Furthermore, today's fitness industry does not even generate or collect the type of data needed to calculate proper recovery periods, let alone have the equipment or business method and system to support it. The condition of the fitness industry is such that accurate data and repeatable data are not available. Industry sources report that fitness equipment, in general, is not accurate within fifty percent. Some manufactures are even clearer, e.g., "makes no representations or warranties of any kind, with respect to merchantability of fitness or suitability for any general or particular purpose, or of the results anticipated or experienced in the use of such equipment, specifically including but not limited to the accuracy or inaccuracy of any data provided by the equipment."

The failure of existing fitness programs is clear and is evidenced by the fact that even the most dedicated fitness enthusiasts will often fail in their efforts to maintain fitness and strength. Common reasons for failure include schedule conflicts with personal and professional commitments, poorly contrived exercise routines producing disappointingly slow or limited progress, the inherent limitations of existing home exercise equipment, the often-overwhelming inconvenience or inadequacy of the local fitness facility, and perhaps the most serious, frequent and disabling injuries.

Given the above background, what is needed in the art are improved systems and methods for implementing exercise programs.

SUMMARY

One aspect of the present disclosure provides an improved exercise program designed to increase individuals' strength and overall fitness while minimizing the number of exercise-related injuries they may suffer in the process. Provided are components that collectively decrease the number of exercise related injuries. Such components include, but are not limited to, (i) fully contracted exercises that utilize custom designed, solid state exercise equipment; (ii) mandatory recovery periods between equipment use; (iii) collection of medical and physiological information before exercise participation; (iv) collection of the exercise results and the use of such data to calculate an appropriate recovery time; (v) central processing of an exerciser's incremental exercise results for the purpose of performance tracking as well as the calculation of mandatory recovery periods; and (vii) provision of timely feedback and recommendations for customization of individualized exercise programs. These components work together to produce an individualized, optimized and safe muscle tissue development and fitness program, termed a fully contracted model, in accordance with an aspect of the present disclosure.

As noted above, an aspect of the present disclosure makes use of a mandatory recovery period. Among other advantages, this mandatory recovery period prevents injuries, and optimizes the body's ability to develop skeletal muscle. Rest and recovery are essential to injury free, successful exercise. This is particularly true in strength building. Berardi and Mejia, in *Scrawny to Brawny: The Complete Guide to Building Muscle the Natural Way*, Rodale Inc., 2005, hereby incorporated by reference in its entirety, state that it takes about seven to fourteen days for the body's immune system to rebuild muscle fibers broken down during exercise. More importantly, during this process these muscle fibers are rebuilt even stronger than the fibers that existed before exercise began.

The present disclosure further provides convenient scheduling and personal training in a private setting, utilizes full contractions on solid state fitness equipment, and analyzes the exerciser's medical information so that the proper amount of muscle tissue recovery and development time can be determined for each exerciser at every appointment. By providing for a mandatory recovery time between exercise appointments and custom-tailoring, the length of the recovery time is adjusted to the physiological needs of the individual. As such, the systems and methods of the present disclosure ameliorate the increasing problem of exercise-related injuries.

In addition, by utilizing the fully contracted model, also known as the maximum static contraction method, as a primary exercise regimen, this disclosure provides a convenient and effective exercise program for its participants, as with this positioning of optimal biomechanics, maximum loads can be attained. In 2004 the Surgeon General's Report on Bone Health and Osteoporosis (See, Chapter 9) stated; "Increases in bone mineral density, to prevent or reverse the effects of osteoporosis, are stimulated by maximum loading on the musculoskeletal system." Furthermore, Zatsiorsky and Kraemer and in their 2006 book, *Science and Practice of Strength Training* (P. 50), explain the difference between the two different types of muscular growth; "sarcoplasmic hypertrophy of muscle fibers is characterized by the growth of sarcoplasm (semifluid interfibrillar substance) and non-contractile proteins that do not directly contribute to the production of muscle force." Stated differently, sarcoplasmic hypertrophy happens when an individual engages in physical movement with load applied. This could be lifting weights and also, to a smaller degree, walking. As blood moves into the muscles being used, the blood takes with it proteins, glycogen, and toxins. As the blood leaves after the exercise is over, the proteins, glycogen, and toxins are left behind. This is called "Sarcoplasm." The sarcoplasm does dissipate within a few days or a few months, depending on the individual's health and activity levels. However, myofibril growth, also called myofibril hypertrophy, is different. This is where the central nervous system perceives failure of the muscle to handle specific maximum loads momentarily. This signal forces a much more powerful adaptive response. The actin and myosin, which are the free floating proteins in the muscle cells, then merge to form another actuator, called a myofibril. As these myofibrils build within the single cell, the cell increases in density. This is the more important response, and has a much longer-lasting effect in the body, but more importantly this is how greater amounts of strength are created. The effectiveness of a myofibril stimulus comes from the maximum number of myofibrils being engaged when the failure load is achieved. This adaptive response also has convincingly been shown to improve muscle metabolic efficiency and optimize energy utilization (See, Slentz, Houmard, Kraus, 2009, "Exercise, abdominal obesity, skeletal muscle, and metabolic risk: evidence for a dose response," Obesity, Silver Spring, 2009, Dec. 17, Suppl. 3:S27-33), as well as minimize the inevitable muscle mass loss associated with the normal aging process, which allows for the body to retain more nutrients in later decades of life for normal healthy function (See Kehayias et al. 1997, "Total body potassium and body fat: relevance to aging," American Journal of Clinical Nutrition 66:904-10). Muscle mass maintenance can then indirectly prevent weight gain by maintaining the higher basal metabolic rate associated with this increased muscle mass. The key is a combination of optimal muscle effort to stimulate growth and development while allowing adequate rest for complete recovery. The importance of recovery is emphasized by M. Doug McGuff, MD, *Maximize Your Training*, Brzycki (ed.), McGraw-Hill (1999), hereby incorporated by reference in its entirety, who states "In general, we have found that 7 days of recovery is long enough for most, and is not too long for anyone." The disclosed exercise program facilitates the maximum loading that, in combination with moderate weight loss, was effective in improving glycemic control in older patients with type II diabetes. See Dunstan, et al. "High-Intensity Resistance Training Improves Glycemic Control in Older Patients with Type 2 Diabetes," Diabetes Care 25:1729-1736, 2002. Furthermore, the disclosed exercise program also only requires a minimal amount of the exerciser's time, which is likely to increase the exerciser's long-term commitment to the program.

Thus, prior to the disclosed exercise program and administrative system, there was no science-based, physical fitness system available that combines ultimate safety with convenience and sustainability. This disclosure addresses each and every aspect of strength development from injury reduction and/or elimination, to the retention of exercisers' interest as they progress in the program and their need for physical fitness grows more important year by year.

The present disclosure seeks to change the way that individuals get in shape by providing a new method of strength training that only requires a minimal amount of time and virtually no sweat from its participants. Moreover, this disclosure challenges many of the fitness industry's current trends by creating a sustainable strength training program that appeals to a much broader population base while promising to reduce injury risk factors. This program refutes the premise that injury is implicit to sport while making advances in addressing an important issue in sports medicine—increasing obesity and diminishing fitness in an aging society. This disclosure also aims to teach maturing adults that while a working heart is essential to life, skeletal muscle strength is also needed to enjoy it. Consequently, the systems and methods in accordance with the present disclosure target individuals interested in improving their health and fitness, but unsatisfied with existing exercise programs by providing a sustainable, time-efficient, and safety-conscious alternative to conventional fitness programs.

To achieve the aforementioned goals, the systems and methods of the present disclosure utilize a relatively new muscle-building concept known as the "fully contracted" method, or the maximum static contraction method, to help exercisers build skeletal muscle strength. Unlike conventional programs that implement highly repetitive resistance training (using free weights) programs, this disclosure's fully contracted methodology uses relatively infrequent maximum muscle contractions to build skeletal muscles. Furthermore, this fully contracted exercise regimen, in which specific muscle groups are brought to full contraction, is followed by a new rest and recovery technique that is monitored by the disclosure's custom software and central data processing system.

Exercisers in this program perform any combination of at least four different fully contracted exercises: bench presses, leg presses, core pulls, and vertical lifts. All of these exercises are performed on solid-state custom exercise equipment. For the purposes of this disclosure, "solid-state" equipment means exercise equipment that has few or no moving parts. In other words, unlike traditional exercise equipment, solid-state equipment does not require an exerciser to lift blocks of weights up and down. Rather, exercisers in accordance with the present disclosure create pressure on the equipment while either sitting or standing. As the pressure increases, the exerciser must hold the position as long as possible. The exerciser releases the equipment when their muscles can no longer withstand the pressure. After the equipment is released, the final force exerted by the exerciser is determined and used as a basis for future exercises.

One of the advantages of the present disclosure is use of the principle of placing extreme stress on a particular fully contracted muscle group in order to make the muscle group stronger when it regenerates. Therefore, the momentary muscle failure experienced by an exerciser's experience in this static contraction program is, in fact, just a means of stimulating the exerciser's muscles to develop and grow.

Optimal muscle development is central to the purpose of the program, improved strength and fitness for its exercisers. This program takes as its premise the principle that muscle mass at rest burns more calories than fat or non-muscle tissue. In fact, if one gains ten pounds of muscle, this extra muscle will burn the caloric equivalent of running five miles a day, seven days a week. Thus, by participating in this muscle building program, exercisers will essentially be able to concomitantly increase both their muscle mass and their metabolic rate.

However, in order to achieve optimal muscle development, the systems and methods of the present disclosure also utilize strategic rest periods between exerciser's exercise appointments. In order to attain the optimal rest period, this program relies on its custom software programs to analyze each exerciser's performance and determine how much recovery time is needed. An important aspect of the present disclosure is optimization of the rest interval between exercises in order to allow muscles to properly rehabilitate without the threat of injury.

Taking into account an average rest period, exercisers enrolled in a program in accordance with the present disclosure need only visit an enterprise office once every other week for a few minutes in order to comply with the inventive regimen. Furthermore, exercisers typically do not even have to change into exercise clothing in order to engage in the program because the exercises in accordance with the present disclosure typically do not cause a person to break a sweat. Thus, the inventive program requires a substantially smaller time commitment than many known exercise programs. Therefore, a large number of people who were unable to stay committed to such known fitness programs will benefit from the exercise regimens of the present disclosure.

In addition to identifying the optimum rest period for each exerciser, the unique equipment, software, and central data system disclosed herein are also components of an overall administrative system. For instance, the equipment described herein accurately collects exercise results. Such results can be viewed on a graphical display during the exercise appointment and/or any time after the appointment via an enterprise website. This data is also used to identify the optimum exercise regimen for the exerciser's next exercise appointment, including maximum force and the optimum amount of time the exerciser should wait before the next exercise session.

In addition to facilitating appointment scheduling, the centralized processing system offered in embodiments of the present disclosure also fully supports internal physiological research, administration of the enterprise, electronic billing and merchant banking, and further allows a plurality of exercisers in disparate locations (e.g., across town, state, or country) to have their medical information encrypted and treated confidentially.

One aspect of the present disclosure provides a method of facilitating a fully contracted exercise regimen for a subject. The method comprises developing one or more exercise constraints as a function of the medical health information of the subject. Next, the subject performs a plurality of exercises in which specific muscle groups are brought to full contraction using exercise equipment in the presence of a fitness trainer thereby producing a set of exercise results. The exercise equipment has one or more strain gauges in order to impose or monitor exercise constraints in the one or more exercise constraints. A mandatory recovery period is imposed for the subject after performing the plurality of contraction exercises during which time the subject does not perform the contraction exercises. The exercises interspersed between mandatory recovery periods are repeated using a new set of one or more exercise constraints that are refined based upon previous exercise results. In preferred embodiments, the fitness trainer is not assigned to any other subjects when the subject is performing exercises supervised by the fitness trainer.

Still another aspect of the present disclosure provides a computer program product for use in conjunction with a computer system. The computer program product comprises a computer readable storage medium and a computer program mechanism embedded therein. The computer program mechanism comprises instructions for receiving medical health information of a subject enrolled in a fully contracted exercise regimen. The computer program mechanism further comprises instructions for developing one or more exercise constraints as a function of the medical health information of the subject. The computer program mechanism further comprises instructions for receiving an exercise result from a plurality of fully contracted exercises that were performed by the subject using exercise equipment in the presence of a fitness trainer. The exercise equipment has a strain gauge in order to impose or monitor exercise constraints in the one or more exercise constraints. Data from the strain gauge is found in the exercise result. The computer program mechanism further comprises instructions for creating a mandatory recovery period for the subject after the subject has performed the exercises. The exerciser does not perform fully contracted exercises during this recovery period. The computer program mechanism further comprises instructions for repeating the aforementioned instructions using a new set of one or more exercise constraints that were refined based upon previous exercise results.

Yet another aspect of the present disclosure provides a computer system for facilitating a fully contracted exercise regimen for a subject. The computer system comprises a central processing unit and a memory, coupled to the central processing unit. The memory stores a computer program mechanism. The computer program mechanism comprises instructions for receiving medical health information of a subject enrolled in a fully contracted exercise regimen. The computer program mechanism further comprises instructions for developing one or more exercise constraints as a function of the medical health information of the subject. The computer program mechanism further comprises instructions for receiving an exercise result from a plurality of fully contracted exercises that were performed by the subject using exercise equipment in the presence of a fitness trainer. The exercise equipment has a strain gauge in order to impose or monitor exercise constraints in the one or more exercise constraints. The data from the strain gauge is found in the exercise result. The computer program mechanism further comprises instructions for creating a mandatory recovery period for the subject during which time the subject does not perform fully contracted exercises. The computer program mechanism further comprises instructions for repeating the instructions for receiving, and the instructions for creating using a new set of one or more exercise constraints that were refined based upon the exercise results of a previous instance of the instructions for receiving.

Still another aspect of the present disclosure provides an exercise apparatus for facilitating a fully contracted exercise regimen for a subject. The exercise apparatus comprises a casing, a strain gauge housed within the casing, a central processing unit housed within the casing, and a memory housed within the casing, coupled to the central processing unit, the memory storing a computer program mechanism. The computer program mechanism comprises instructions for receiving one or more exercise constraints. The one or more exercise constraints are determined as a function of the medical health information of the subject by a remote computer. The computer program mechanism further comprises instructions for computing an exercise result from a fully contracted exercise that was performed by the subject using the exercise apparatus in the presence of a fitness trainer. The exercise apparatus uses the strain gauge in order to impose an exercise constraint in the one or more exercise constraints. The computer program mechanism further comprises instructions for sending the exercise result to the remote computer as well as instructions for repeating the aforementioned instructions using a new set of one or more exercise constraints such that the set of one or more exercise constraints are refined based upon the exercise results of a previous instance of the instructions for computing. Furthermore, the instructions for repeating are performed after a mandatory recovery period for the subject that was determined by the exercise result of a previous instance of the instructions for computing.

BRIEF DESCRIPTION OF THE DIAGRAMS AND DRAWINGS

The present invention has many advantages and features that will be more readily apparent from the diagrams, drawings, descriptions, and claims that follow.

Figure 1:
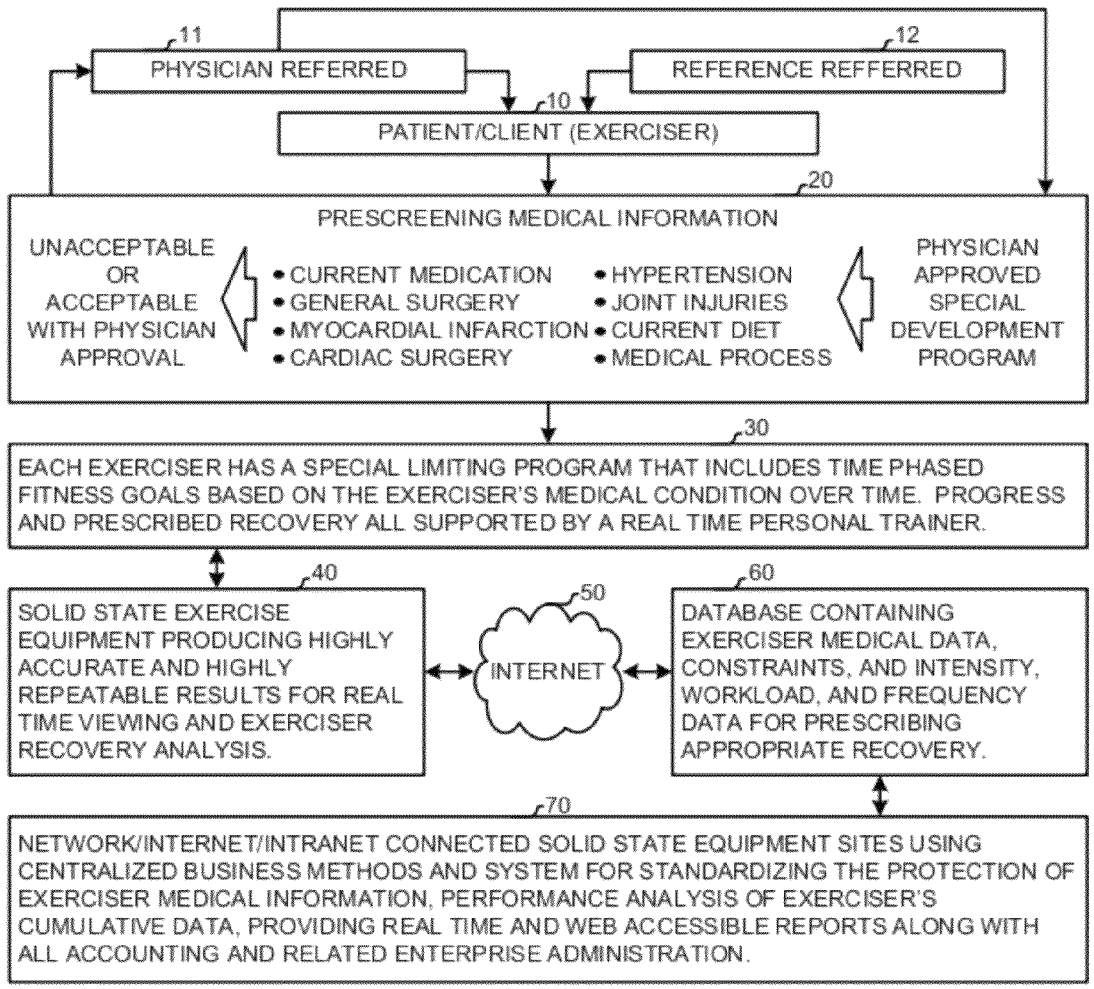
FIG. 1 illustrates a method for providing exercisers with improved health and fitness through increased muscle strength that is achieved without the risk of injury in accordance with an embodiment of the present disclosure.
Figure 5:
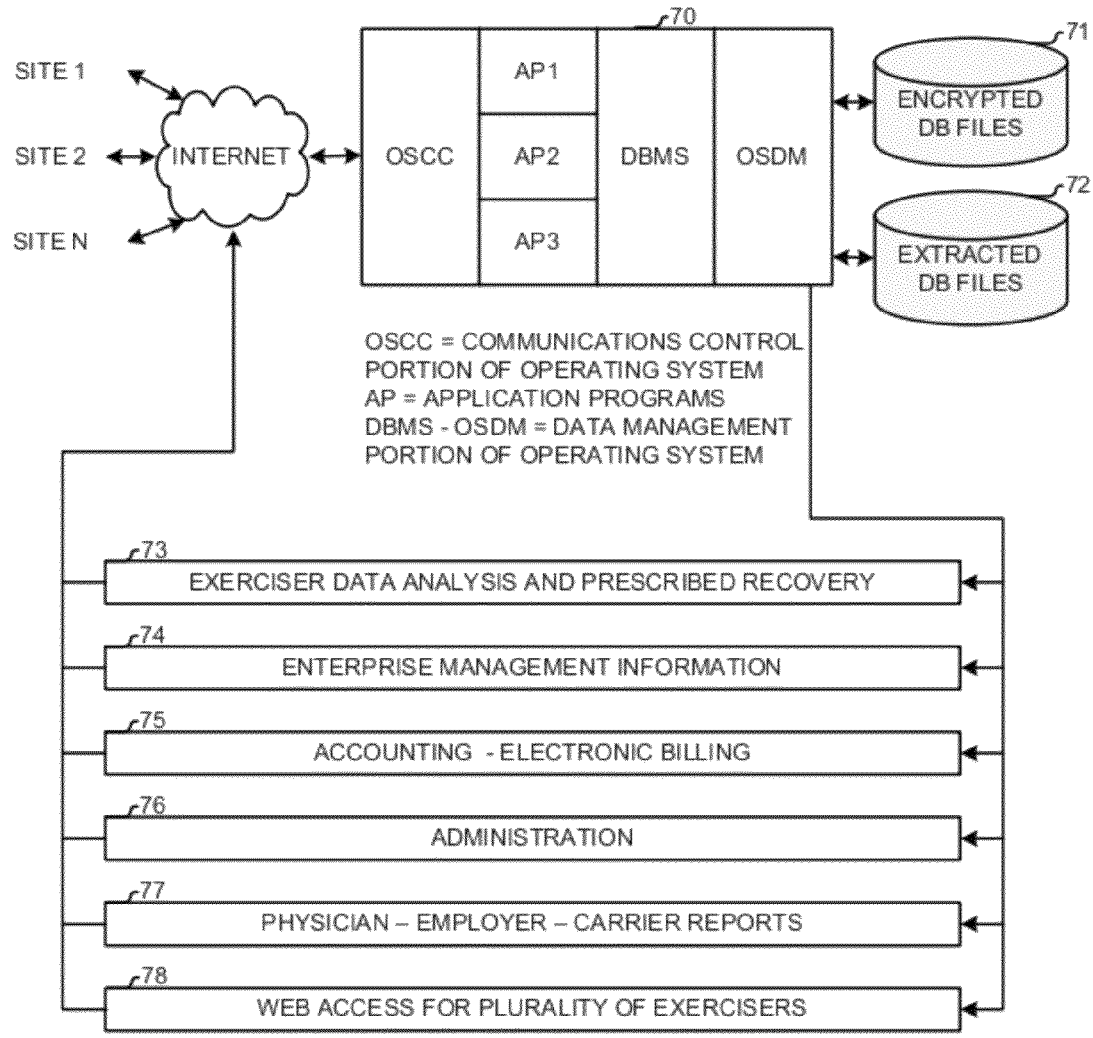
Figure 6A:
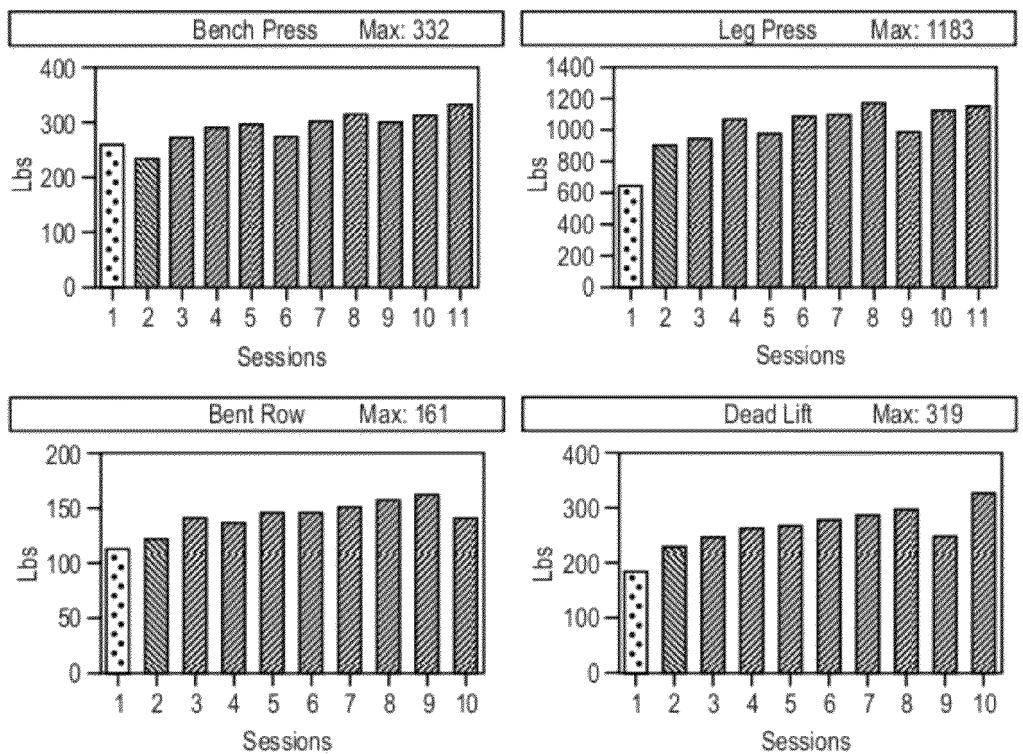
Figure 6B:
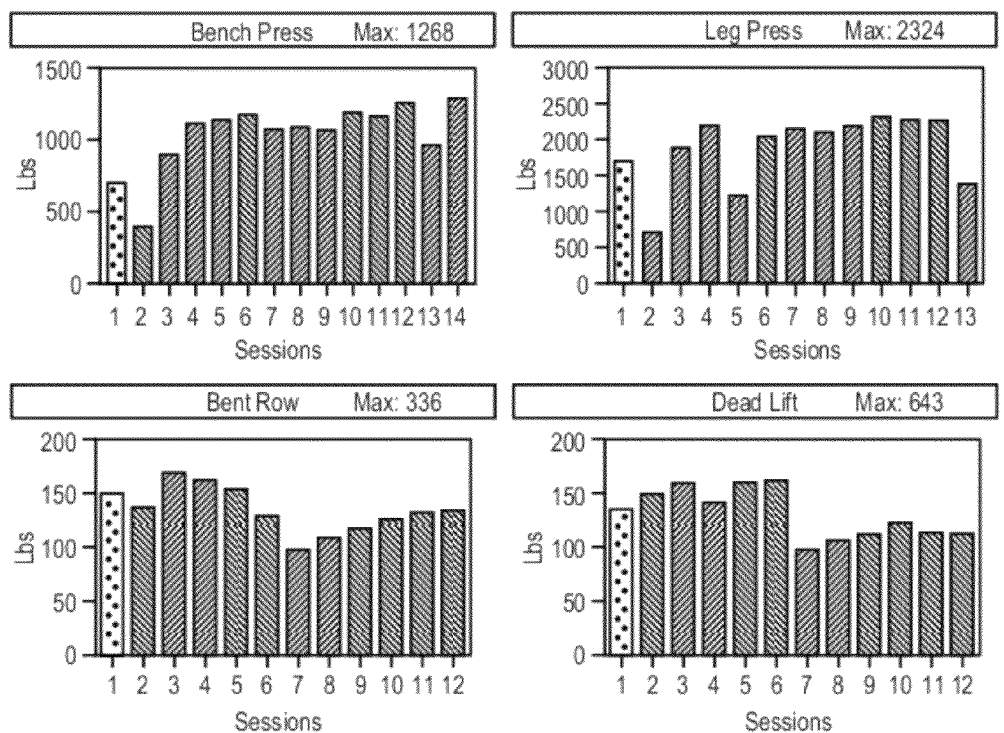
Figure 6C:
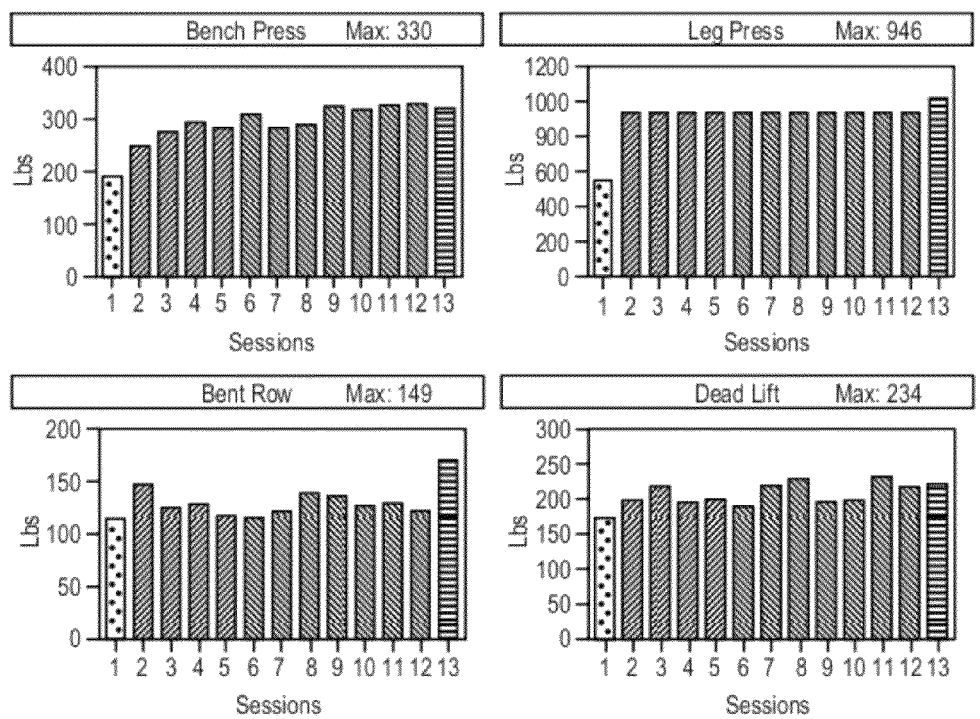
Figure 6D:
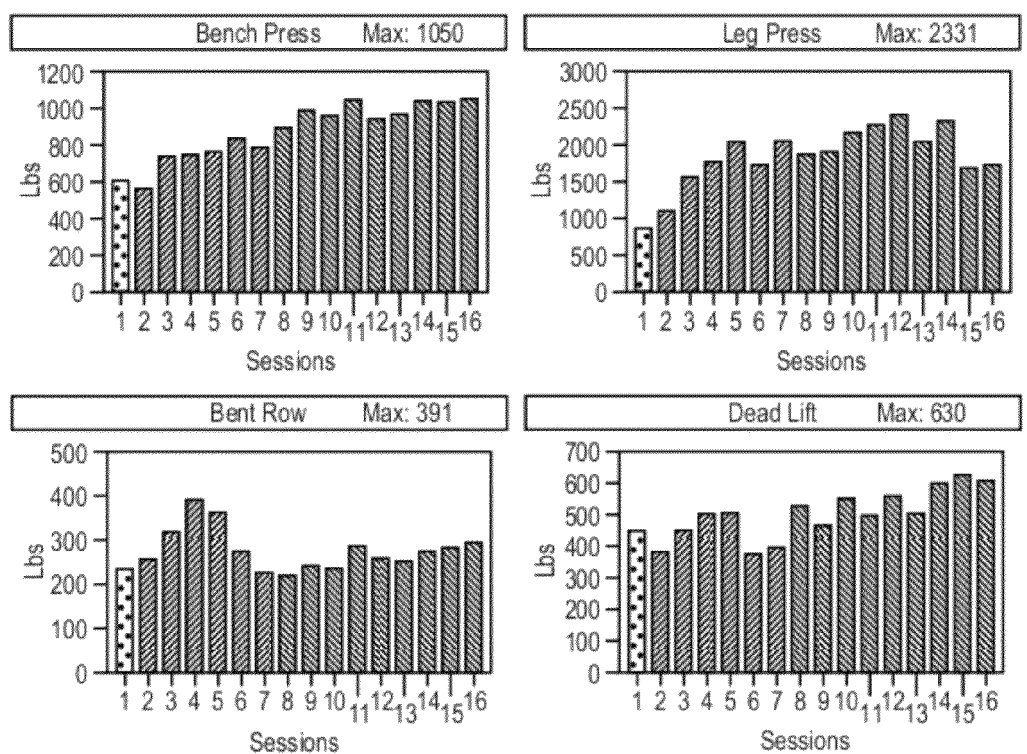
Figure 6E:
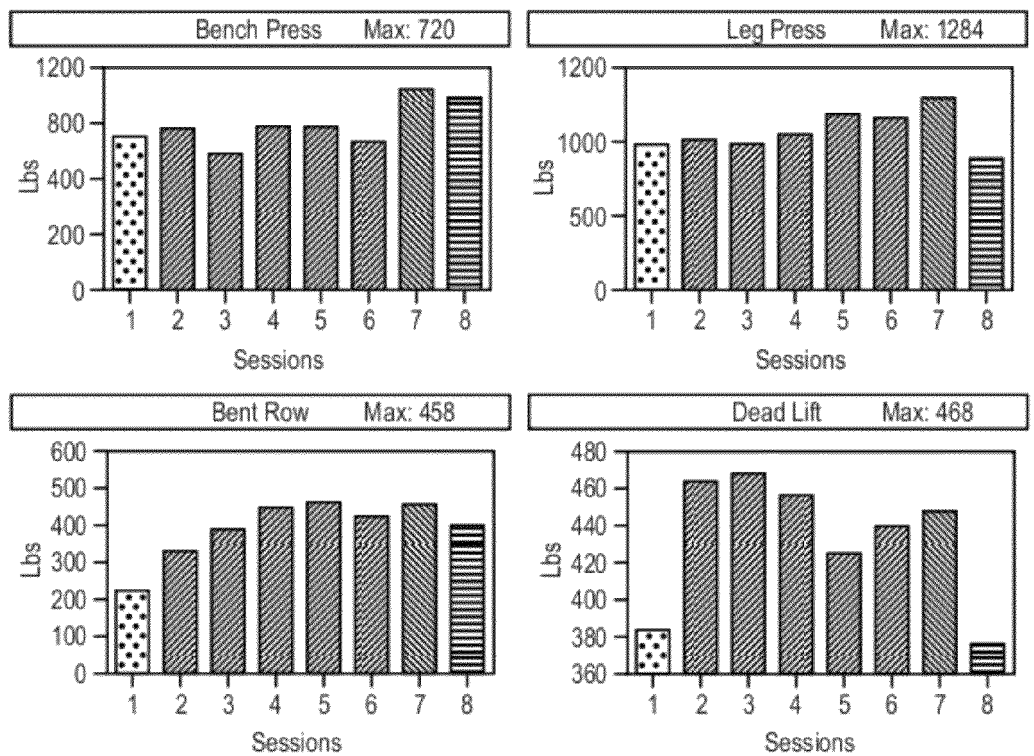
Figure 6F:
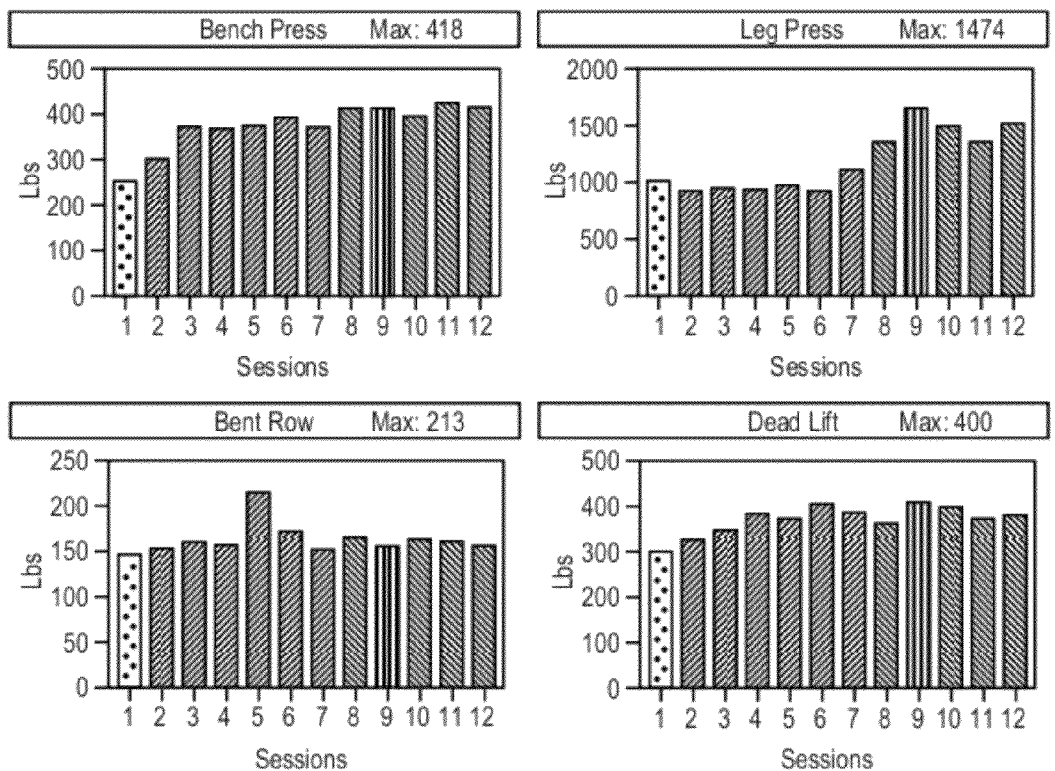
Figure 6G:
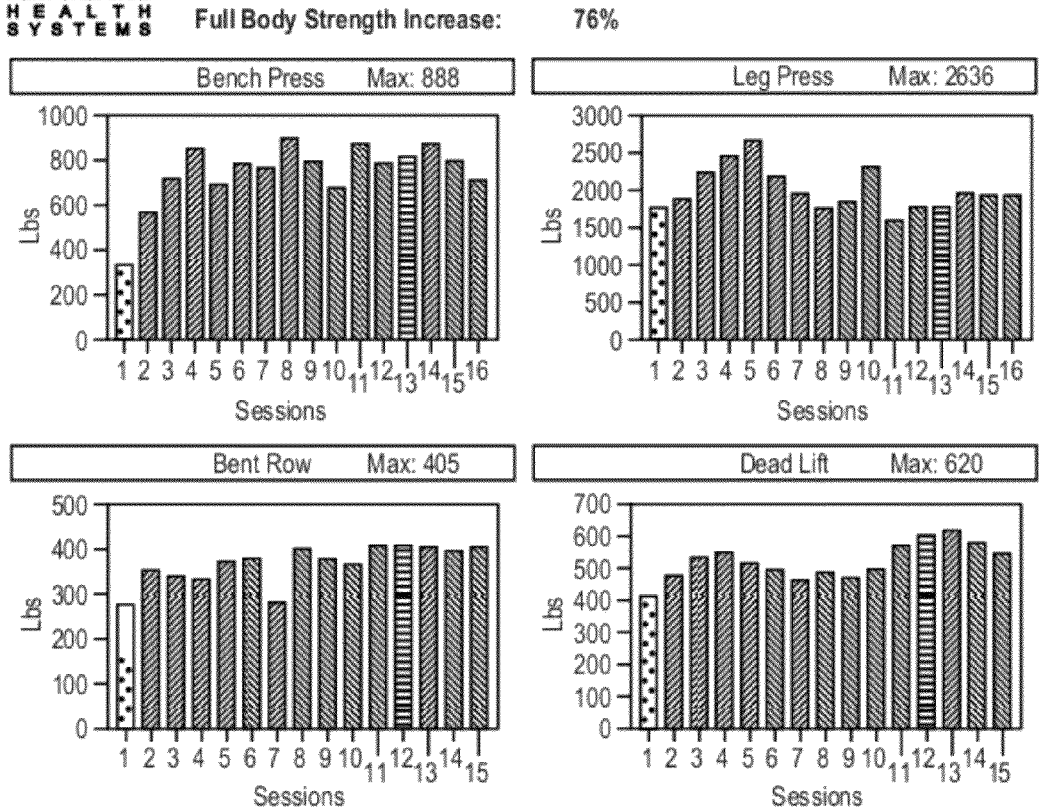
Figure 6H:
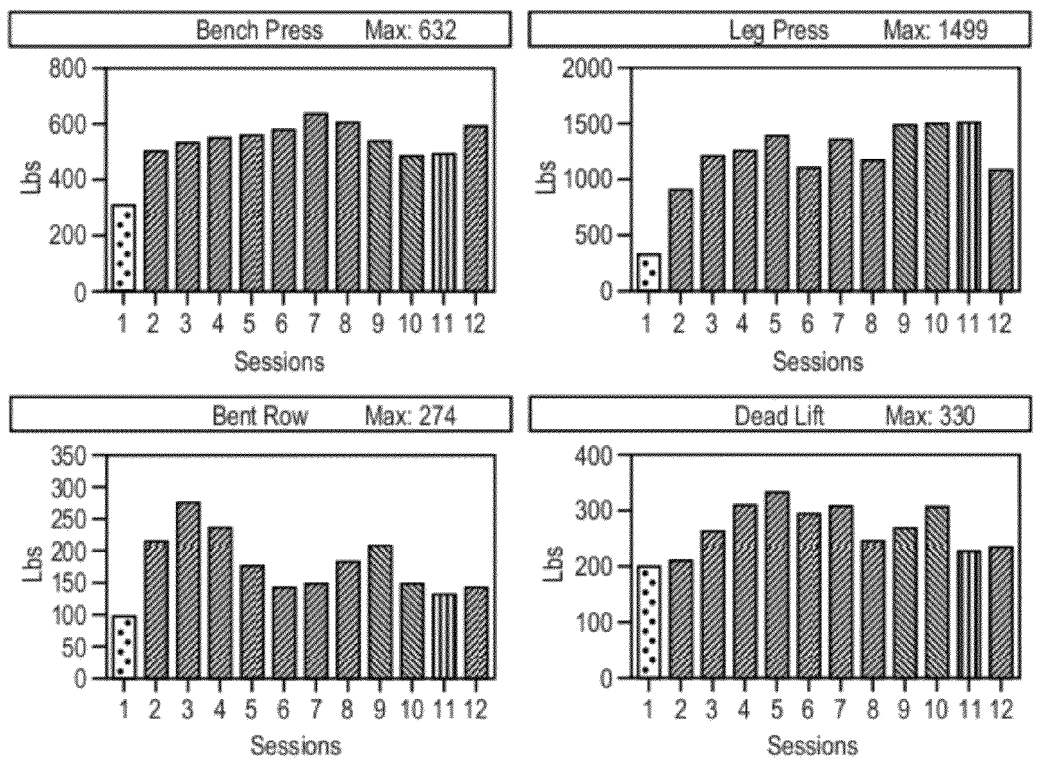
Figure 6I:
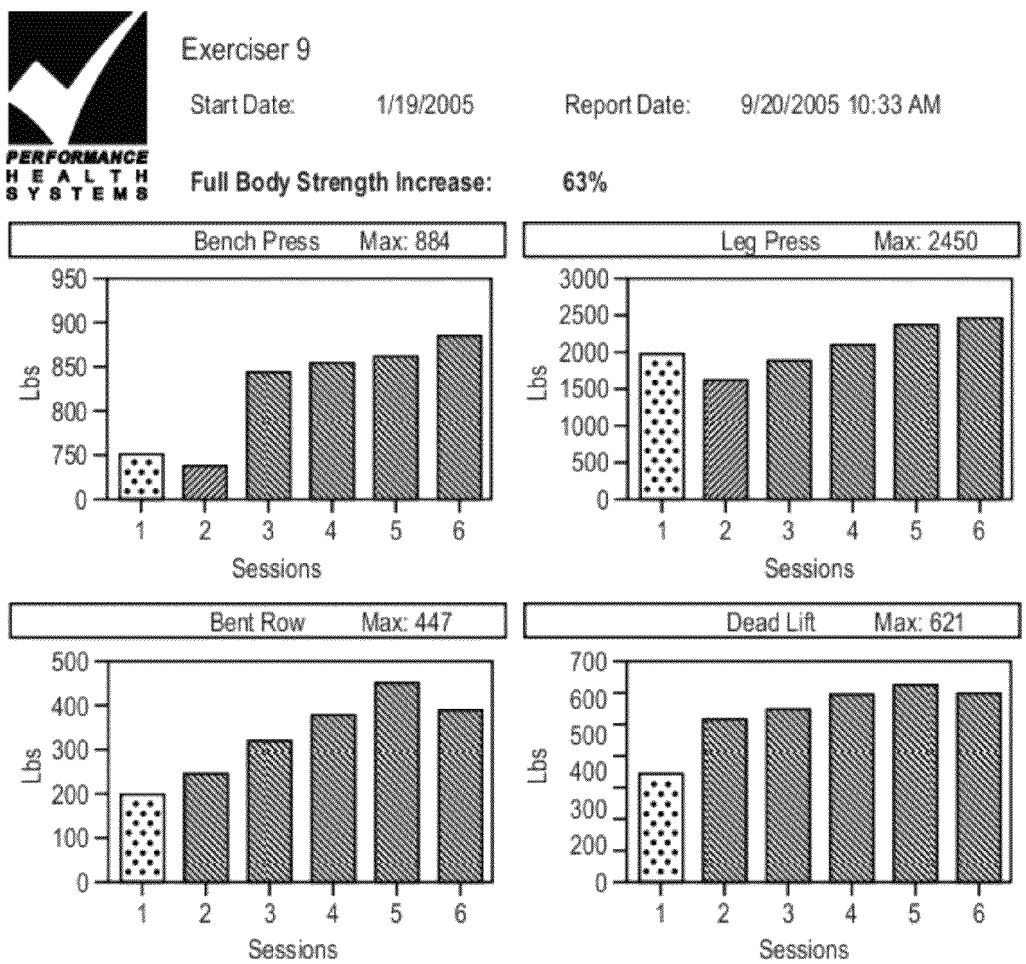
Figure 6J:
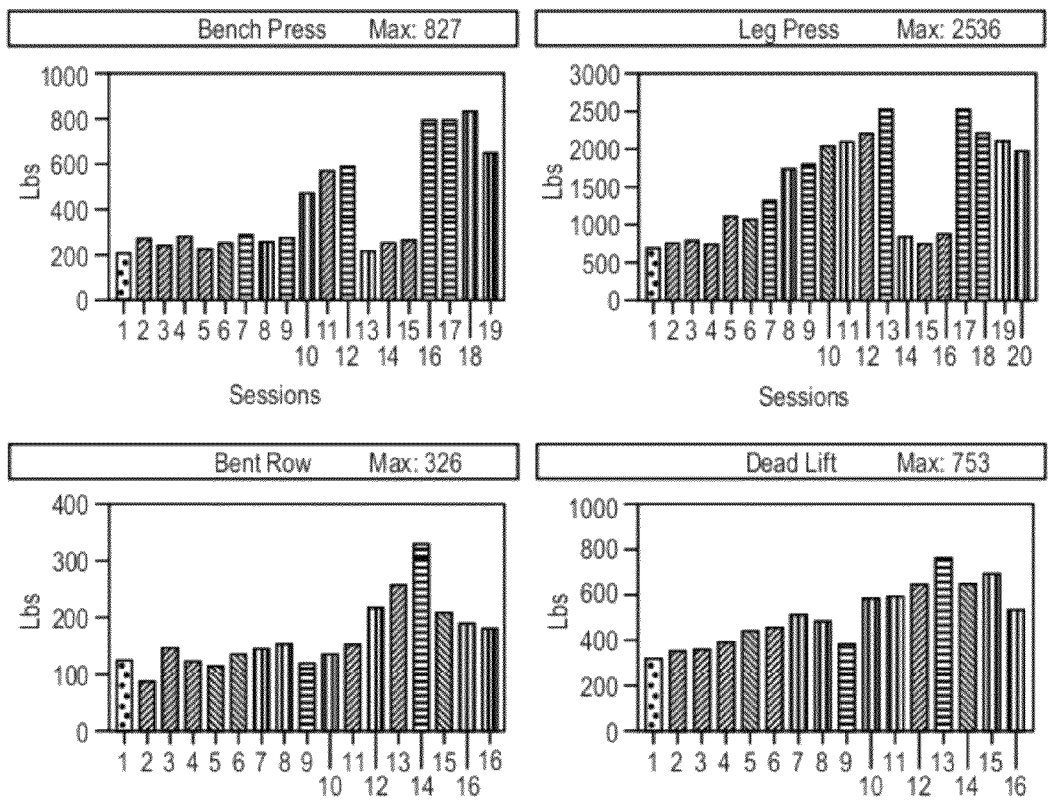

FIG. 5 is a diagram that shows a centralized business information processing and business administration system, providing medical information privacy to exercisers, progress information to exercisers, enterprise information, accounting, and administrative support from the network/Internet/Intranet connected facility shown in FIG. 1, while also providing appropriate exerciser information to physicians, employers, and insurance carriers.

FIGS. 6A-6J illustrates exercise results for individual exercisers that have used the systems and methods of the present disclosure.

Figure 7:
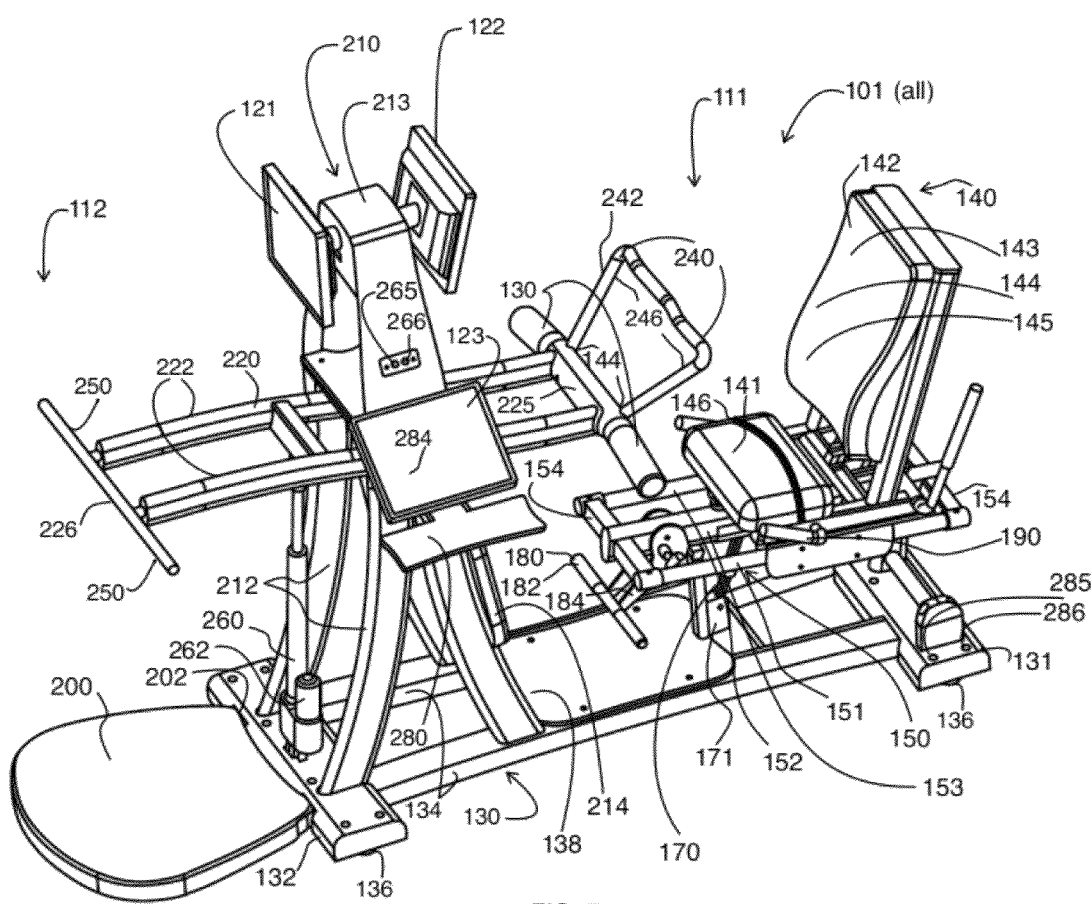
Figure 8:
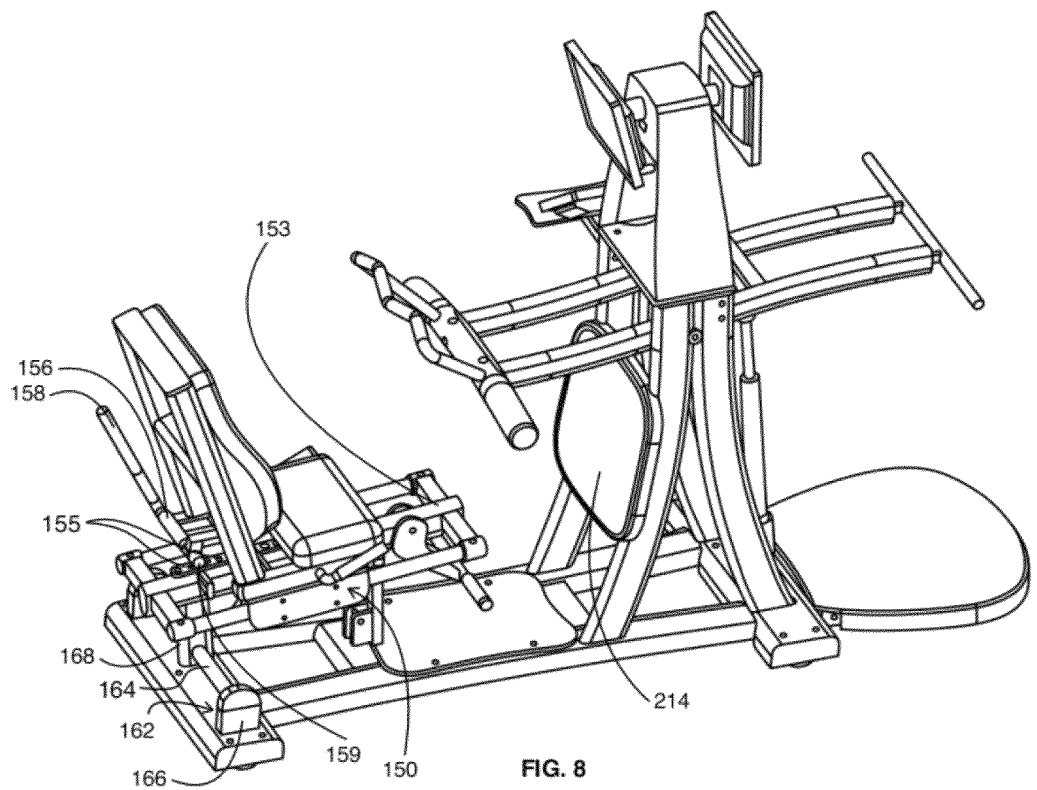

FIGS. 7-8 are perspective views of an exercise machine that are suitable for use with the system illustrated in the previous figures.

Figure 9:
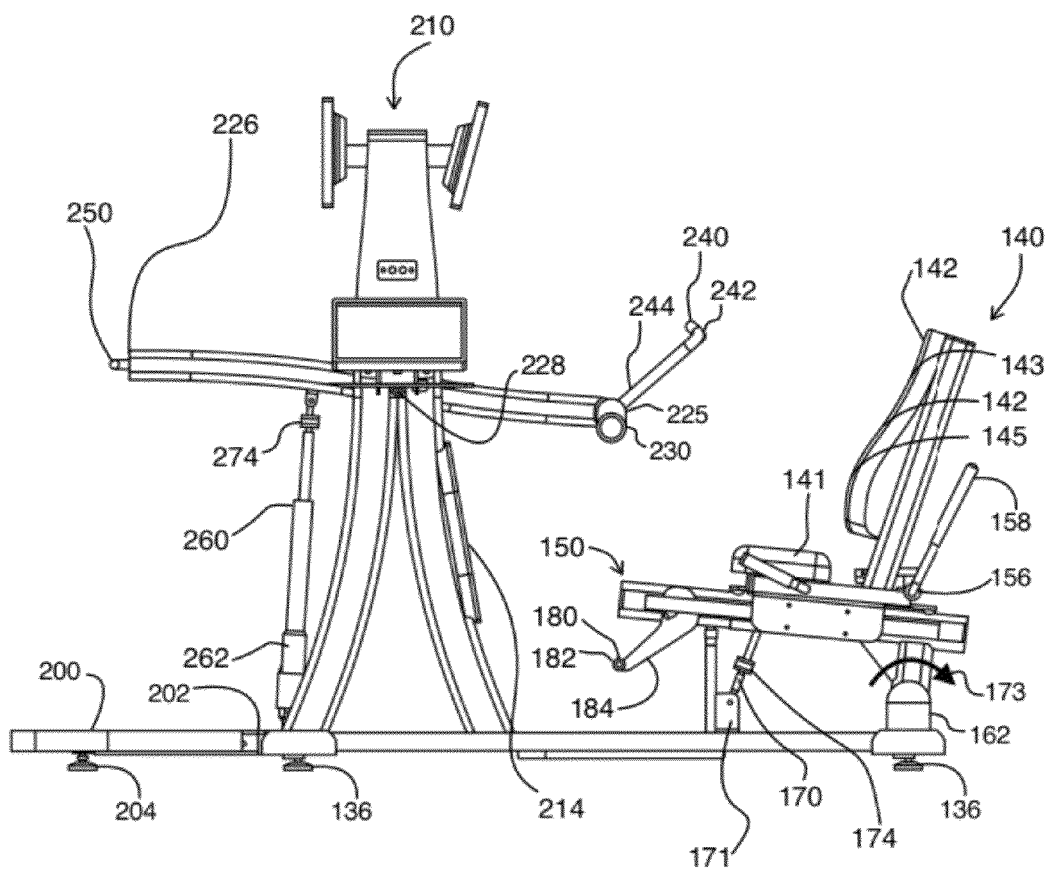

FIG. 9 is a side view of the exercise machine shown in FIGS. 7-8.

Figure 10:
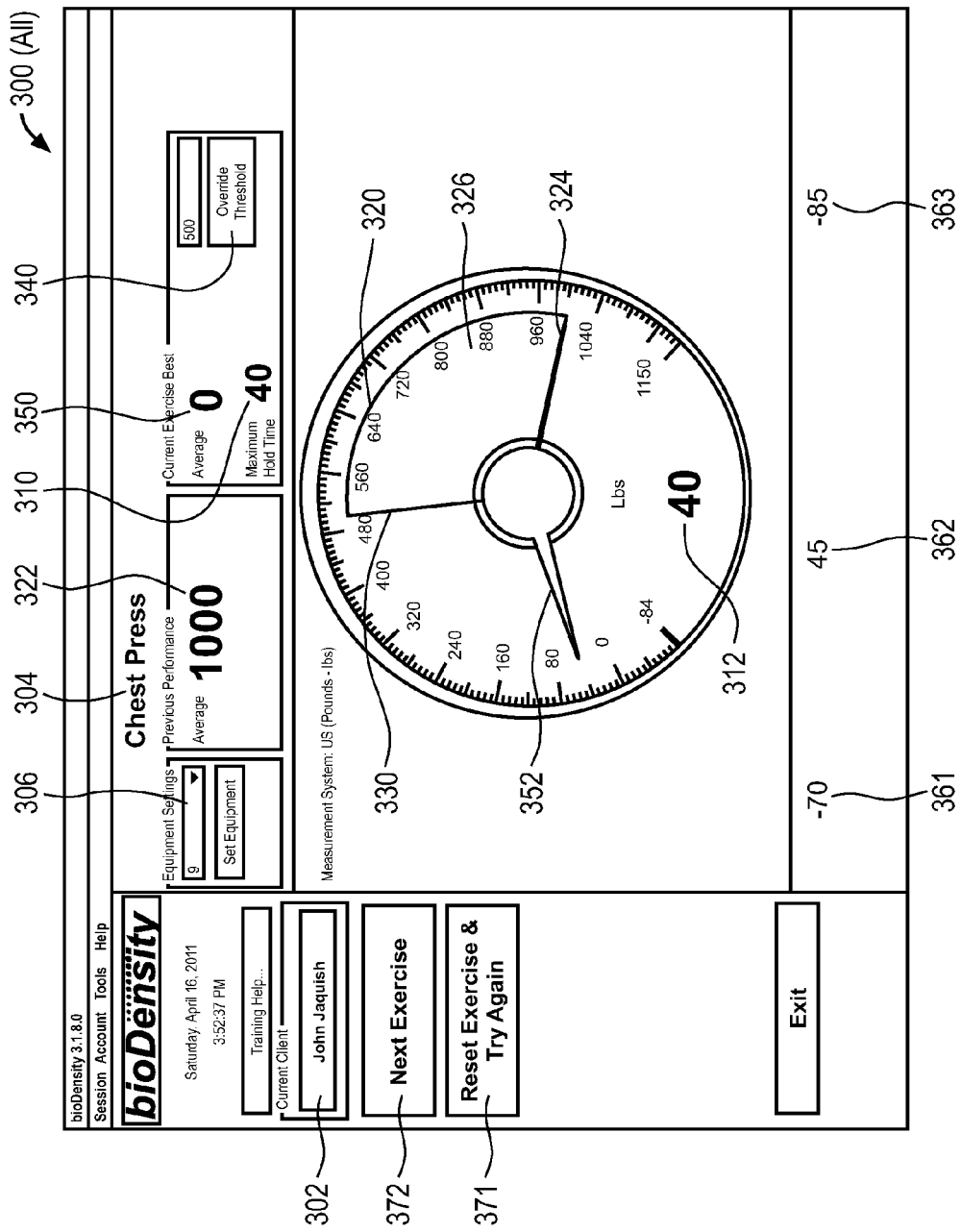

FIG. 10 is screen shot from a display of the exercise machine.

Figure 11:
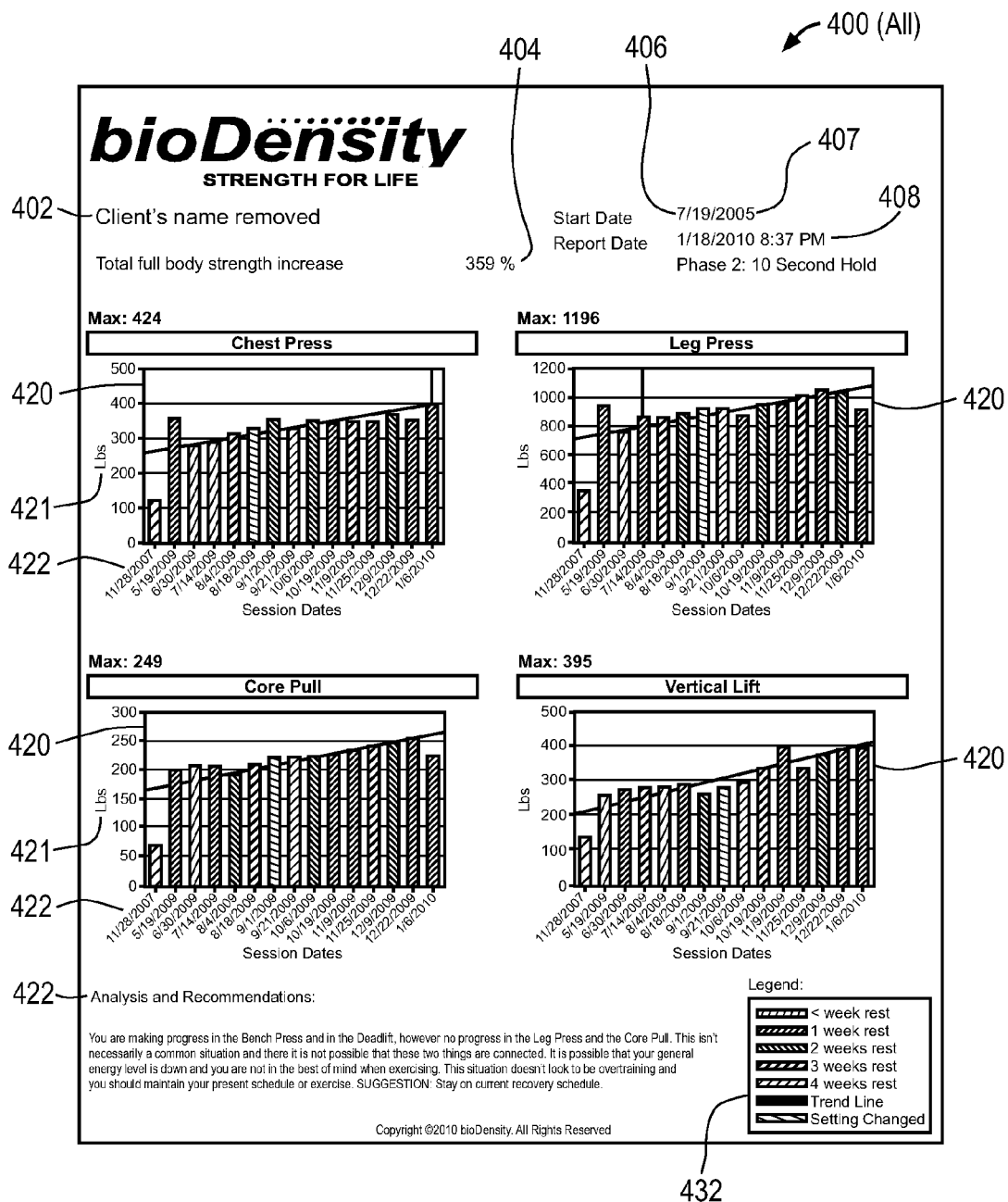

FIG. 11 shows a printout that is printed by the exercise machine at the end of an exercise session.

Figure 12:
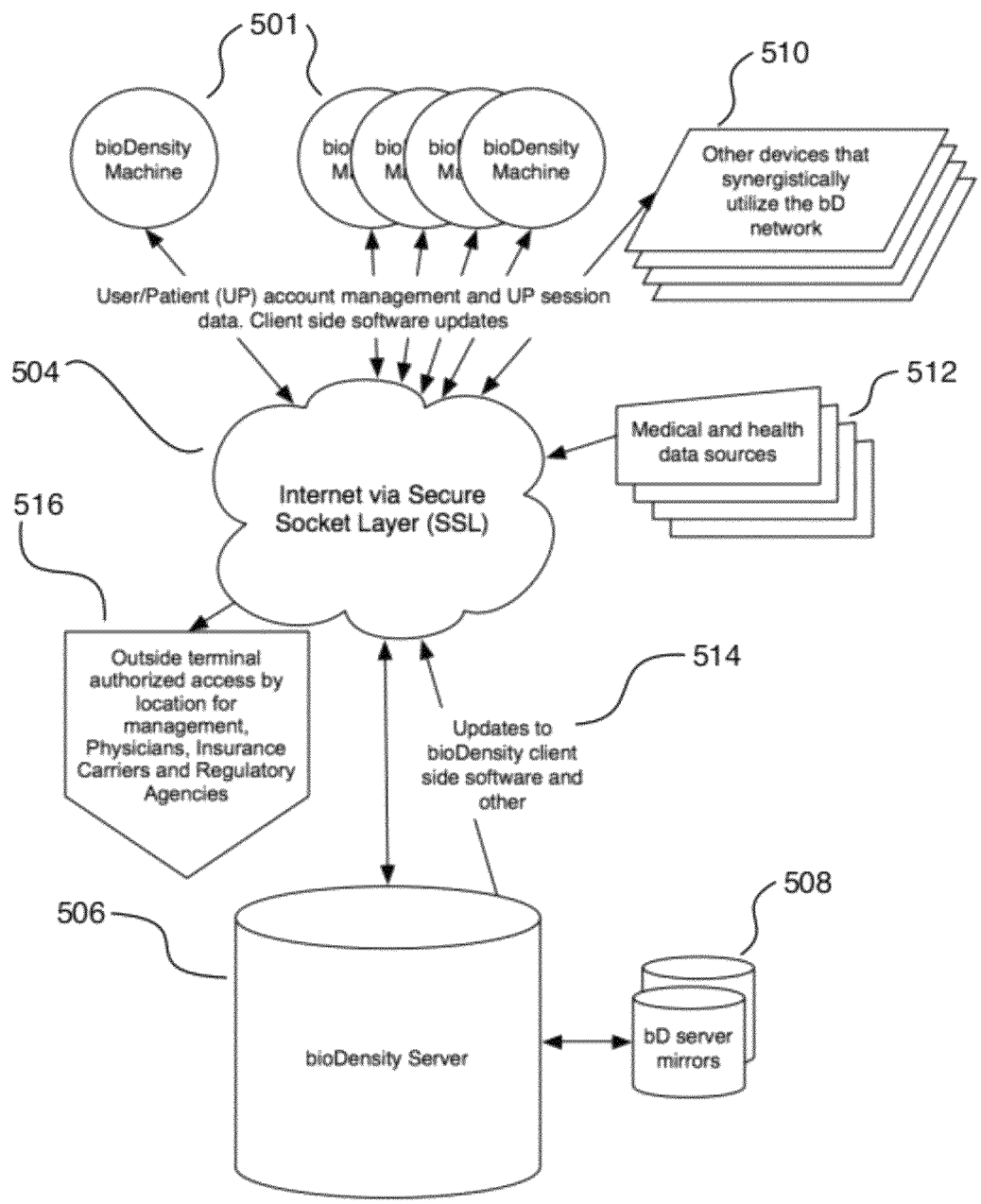

FIG. 12 is a diagram illustrating communication pathways between different components of the system.

DETAILED DESCRIPTION

Embodiments of the present disclosure are explained in the paragraphs that follow. FIG. 1 illustrates novel systems and methods for providing a safer, more sustainable fitness and strength building program for exercisers 10. In this new exercise program an exerciser's health risk factors are determined and then a unique fitness regimen 30 is fashioned for the exerciser 10 based on the exerciser's current state of health, their medical condition and disease situation. Each individualized exercise regimen 30 utilizes custom-designed, solid-state exercise equipment 40 designed to reduce exercise related injuries.

As shown in FIG. 1, in some embodiments prospective exercisers 10 may be referred to this exercise program by a physician 11 or any other recommender 12. Then, as shown in detail in FIG. 2, potential exercisers 10 undergo an initial health risk prescreening process 21 before beginning their exercise regimen 30. In some embodiments, prescreening process 21 is conducted with input from the exerciser's physician 11.

Figure 2:
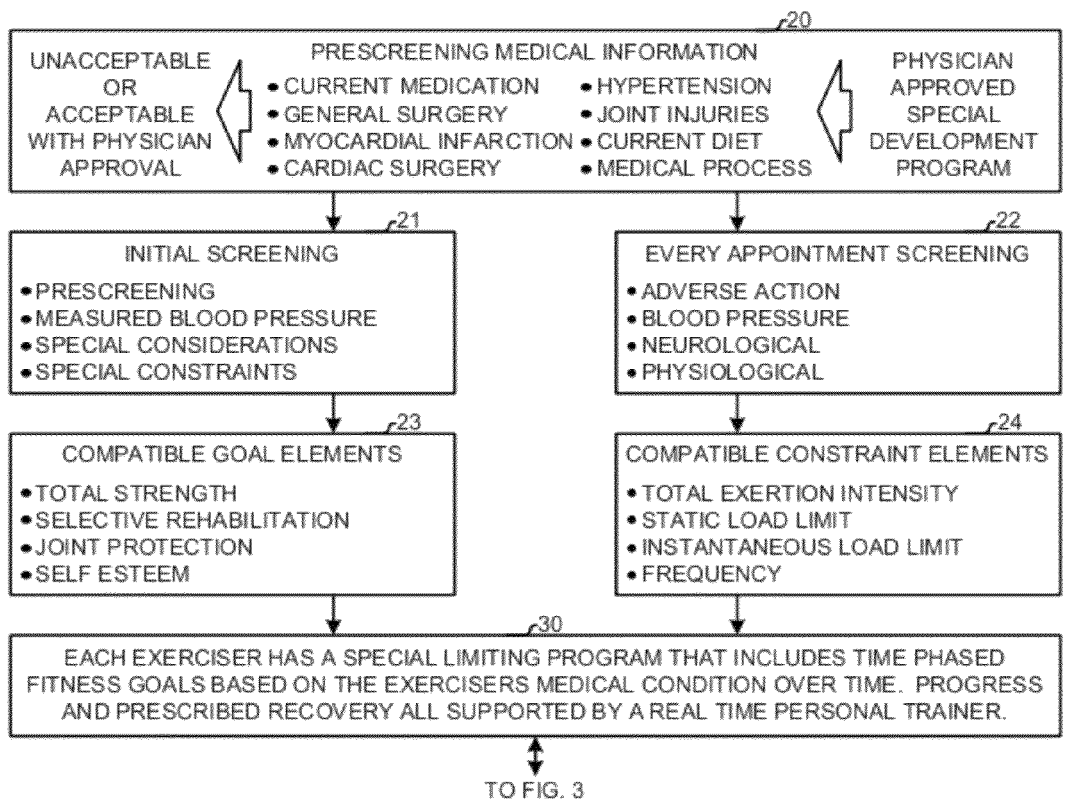
FIG. 2 is a diagram showing a physician-assisted process for setting exercise constraints and goals, where collected medical information dictates, allowing all acceptable exercisers to utilize the system, each with their own exercise program and prescribed recovery in accordance with an embodiment of the present disclosure.

As summarized in FIG. 2, during the initial screening process 21 each exerciser 10 describes any previous injuries to his or her arms, legs and spine, any previous surgery, any previous cardiac difficulties, e.g. arrhythmias (irregular heartbeat), myocardial infarction (heart attack), previous cardiac surgery or other disease or medical condition problems, any previously diagnosis or treatment for hypertension, any medication currently being taken, any current special diet, any nutritional supplements/health food products currently being taken, any unexpected or expected weight changes in the last six months, any sustained injuries while participating in other exercise programs, or any unusual family medical history. Taken together, the exerciser's responses to the aforementioned questions is hereinafter referred to as "prescreening medical information" 20. Furthermore, it will be appreciated that the aforementioned questions are merely exemplary of a broad range of questions that could be asked. Furthermore, not all the aforementioned questions are required in order to obtain a complete set of prescreening medical information 20. Upon completion of this prescreening process 21 and only when needed, some exercisers 10 may also be referred to a physician who can determine what constraints are medically necessary to create a safe and effective exercise program.

As shown in FIG. 2, prescreening medical information 20 and any necessary physician's advice is then used to formulate an individually-tailored exercise regimen 30 for each exerciser 10 that takes into account their physical limitations and/or health risk factors. A set of exerciser-specific exercise limits, hereinafter referred to as exercise "constraint elements" 24, referred to herein also as "exercise constraints," are created in this process. Fitness "goal elements" 23 that are compatible with his or her pre-determined constraint elements 24 are also created in this process. In some embodiments, the exerciser's constraint elements 24 and goal elements 23 are transmitted via a network to a central data processing system 70 (see, e.g., FIG. 5). In some embodiments, this transmission is encrypted.

Referring back to FIG. 2, in some embodiments, each exerciser 10 is also screened on an appointment by appointment basis 22 (also referred to herein as "every appointment screening"). In the optional appointment by appointment screening process 22, each exerciser 10 optionally watches an electronic presentation of certain pertinent health issues prior to exercise participation. In some embodiments, exerciser 10 also answers specific questions during this process, such as: (i) have you sustained any new injuries to your arms, legs, or spine that can impair your ability to engage in the exercise program; (ii) have you experienced any new or different medical problems, including light-headedness or dizziness, that can impair your ability to engage in the exercise program, and (iii) do you have any reason to believe that your blood pressure may have become elevated since your last reliable check, e.g. pounding of your heart, headaches, etc.? Response to question (iii) may also be used to determine whether the exerciser's blood pressure needs be taken before exercising. One embodiment of the present disclosure includes the use of an on-site, automated, clinical quality blood pressure measuring machine to measure the exerciser's blood pressure that is electronically connected to the processing of the exerciser's private medical data.

In some embodiments, each exerciser 10 uses a personal access code to answer specific health questions that are displayed to the exerciser on an electronic display to ensure that the appointment by appointment screening process is completed. Furthermore, as a safeguard, an electronically controlled system also can prevent an exerciser 10 from exercising until all of these questions are answered. In some cases, if any medical problem surfaces during the exerciser's participation in the program, the exerciser may also need to re-enter the prescreening process 21 and provide additional medical information and specific medical evaluations again.

In some embodiments, both the initial prescreening 21 and appointment by appointment screening 22 have injury prevention as their primary objective. As a result, in such embodiments, the exerciser's fitness goals and medical constraints dictate in large measure the characteristics of the customized exercise program developed by the disclosed administrative system.

In some embodiments, fitness trainers or health advisors are optionally present with the exerciser 10 during the exercise regimen. As will be disclosed below, trainers/advisors can perform several functions in this program.

Referring to FIG. 2, in some embodiments, the results of the initial prescreening 21 and/or the appointment by appointment screening process 22 are presented to the personal trainer 30 and exerciser 10 before the exerciser 10 begins a new exercise session. It may also be the personal trainer's 30 job to explain to each exerciser 10 the advantages of this program's technology, equipment, and method of strength training as well as highlight how the present disclosure departs from other typical fitness programs that the exerciser 10 may have used previously. The fitness trainer or health advisor may also assist exercisers 10 and prevent them from inadvertently misunderstanding what they are doing and why, which can result in the exerciser 10 realizing a very high value in this program.

In some embodiments of the present disclosure, exerciser 10 and the associated personal fitness trainer are separated from other exercisers 10 or environmental distractions. For example, they may be situated in a separate cubicle or possibly even in a private room. Such an environment enables the exerciser 10 to be freer to ask questions and conduct exercise training or testing. Providing a real-time personal training regimen 30 in a private setting can also eliminate many of the problems exercisers 10 currently have with the typical fitness industry programs because of the continuous expert oversight/motivation available to the exerciser 10 and the elimination of the social/psychological deterrents of a "gym" or "fitness center" atmosphere.

Figure 4:
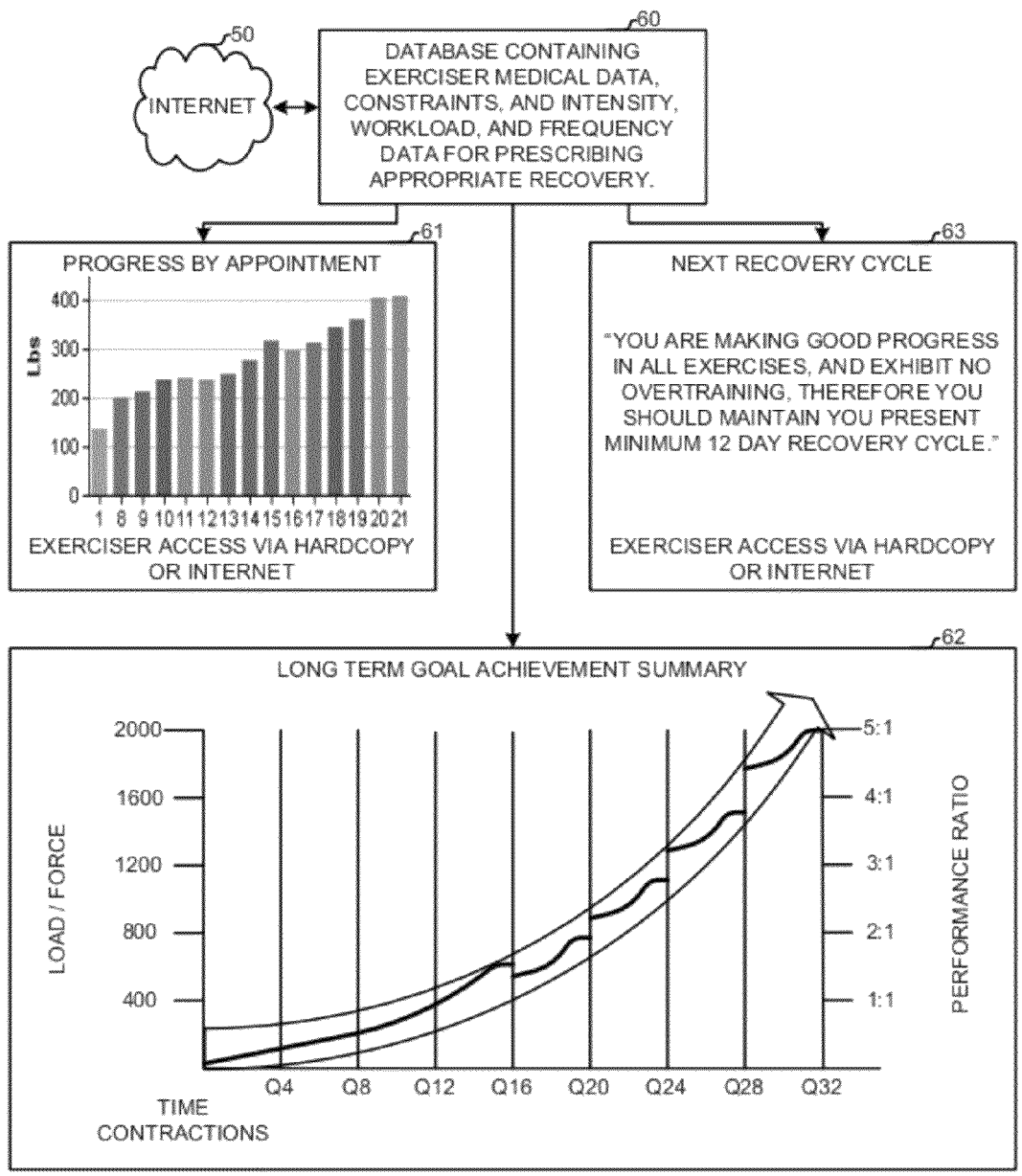
FIG. 4 is a diagram showing a database processing of exerciser medical data constraints, present exercise intensity, load/force, time, frequency and long term goal achievement, as well as the output from recovery specific algorithms, using the medical constraints as shown in FIG. 2 and current exercise data as shown in FIG. 3.

Referring to FIG. 4, in order to ensure the safety of this exercise program, many moving parts have been removed from exercise equipment used in the present disclosure. For example, unlike traditional fitness equipment that is comprised of heavy metal weights, pulleys, cables, springs, levers, chains, etc., all of which are hazards for exercisers 10 using such equipment 40, equipment in accordance with the present disclosure utilizes strain gauges 42 not weights in its structure, and does not have any moving parts that can fall and injure an exerciser 10. Removing the moving parts from this equipment also prevents exercisers from having to adjust the machines without proper instruction, which can often lead to machine misuse, an improper exercise experience, or even injury.

Figure 3:
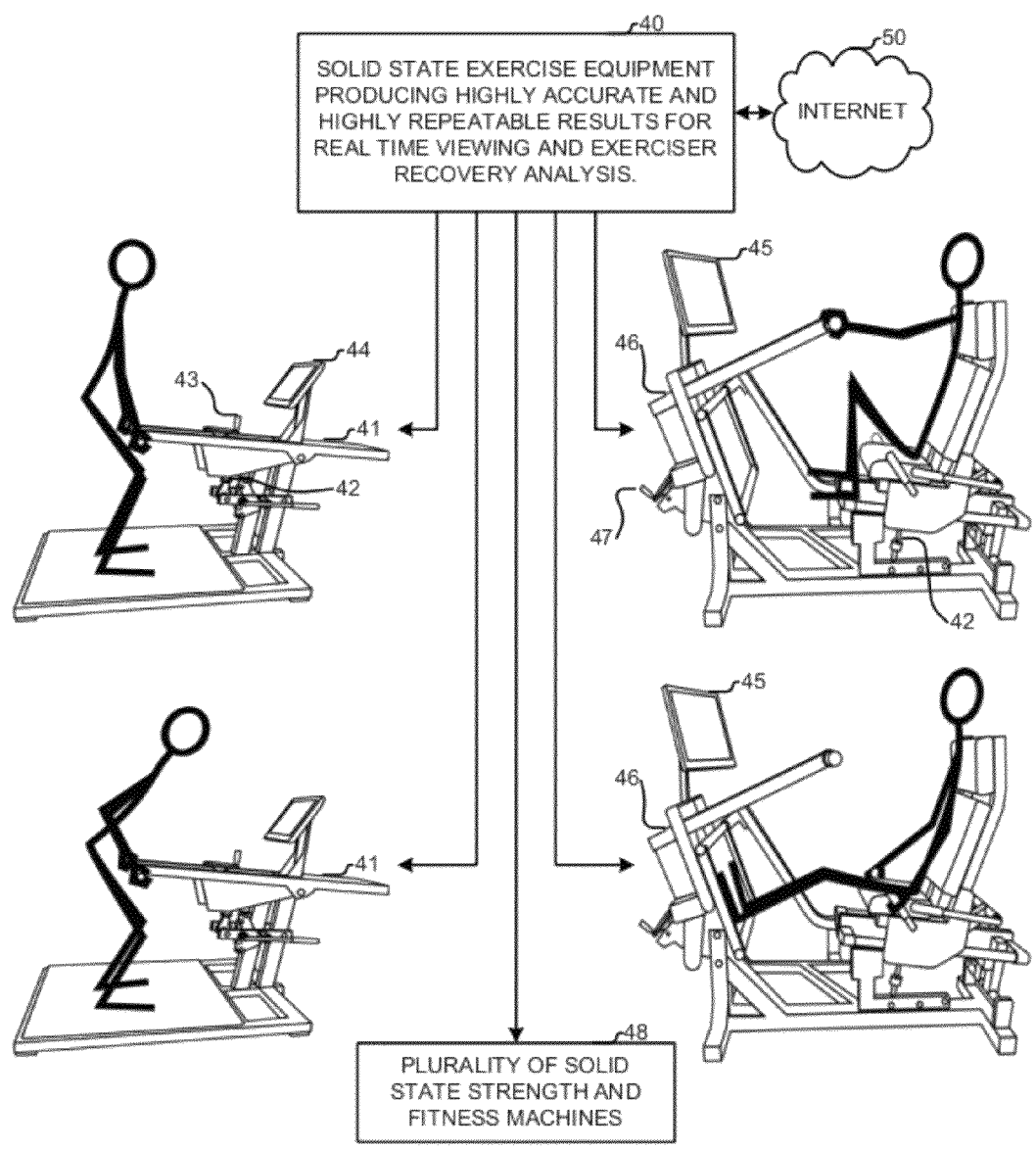
FIG. 3 is a diagram that shows a plurality of solid state exercise equipment sets for collection of individual exerciser data, and the real time display of strength training/testing results in accordance with an embodiment of the present disclosure.

In some embodiments of the present disclosure, exercisers 10 use custom designed, solid state fitness equipment 40, referred herein also as an "exercise apparatus," to exercise. FIG. 3 illustrates several different embodiments of this equipment 41, 46 and also depicts a person performing four of the exercises-vertical lift, core pull, bench press, and leg press— that may be performed on this equipment. Advantageously, the solid state fitness equipment 40 of the present disclosure enables a person to perform these exercises by taking the relevant muscle groups to failure while they are in a fully contracted state. Because fully contracted muscle strength is maximized, in preferred embodiments of the present disclosure solid state fitness equipment 40 withstands 5,000 pounds of exerciser applied load. Further, since no movement is required during the exercises of the present disclosure, solid state fitness equipment 40 must be configured such that exerciser 10 is in a comfortable position at all times in order to maximize the applied loads. Since solid-state fitness equipment 40 are no movement machines, they are configured to accommodate the anatomical differences among exercisers 10. For this reason, a health advisor is present for the exercises conducted in accordance with the present disclosure to make adjustments apart from any action taken by exerciser 10.

Equipment 40 used in the systems and methods of the present disclosure can have any combination of the following features. One such feature is a strain gauge. In some embodiments, this strain gauge is very accurate and makes equipment 40 easily adjustable for different exerciser body types. In some embodiments, this strain gauge is enclosed by adjuster screws 43 for safety. In some embodiments, equipment 40 has the feature of operating without any moving components. In some embodiments, equipment 40 has an electronic display that allows the exerciser 10 and their personal trainer to see, in real time, the exerciser's incremental exercise results. In some embodiments, equipment 40 has the feature of being specially designed to produce highly accurate and reproducible exercise results. In some embodiments, equipment 40 has the feature of being able to produce fitness training/testing results that are approximately ten times more accurate than the current fitness industry equipment. In these embodiments, such results are used to produce each exerciser's individualized exercise regimen 30 and to calculate customized required recovery periods 63 (e.g., FIG. 4).

In some embodiments, both the actual manner in which an exerciser 10 exerts force on equipment 40 during an exercise session and the manner in which these forces are measured, processed and combined with user-specific medical information, produce a result not previously sought by any health and fitness provider and one that is not currently available using traditional fitness equipment or fitness concepts.

In some embodiments, an exerciser 10 begins the exercise program by making an appointment at the enterprise site. In some embodiments, this appointment is conducted in a professional manner and resembles a doctor's appointment in its formality. In some embodiments, the value of the exercise program is discussed with the potential exerciser 10.

If the exerciser 10 finds the information given in the initial appointment satisfactory, they may then choose to sign up for the program. In some embodiments, the exerciser 10 provides certain required general information, which may include health status, prescreening medical information 20, and identification information. In addition to providing health and contact information, the exerciser 10 may also give appropriate billing information for the centralized electronic billing program 75 (FIG. 5). In some cases, exerciser 10 may also need to get a physician's approval to sign up for the program. The first appointment is approximately thirty minutes long in some embodiments. Exerciser 10 is then assigned an administrative identity. In some embodiments, this identity is encoded on an identification card capable of interfacing with the disclosed administrative system.

In some embodiments, a fitness trainer begins to provide exerciser 10 with further instructions and information about the program, including information about the exercise types, equipment 40, data collection methods and recovery periods 63 that comprise this program once the initial appointment is complete. In other embodiments, exerciser 10 schedules a second appointment where he or she will perform the full exercise regimen 30 in the presence of a fitness trainer. In some embodiments, this second appointment is twenty minutes or less.

The exercise regimen 30 utilizes exercises based on the fully contracted method of exercise. The exercises performed in the present invention are heretofore referred to as "fully contracted exercises." A fully contracted exercise is an exercise in which an exerciser positions one or more muscle groups in a fully contracted state and creates an increasing amount of force while the one or more muscle groups are kept in the fully contracted state until the one or more muscle groups fail to create any more force (muscle failure). As such, fully contracted exercises cause a muscle to exert force but do not cause the muscle to change in length. Fully contracted exercises require maximum muscle contraction and require specific muscle groups to create increasing amounts of force until the muscle groups fail to create anymore force.

In some embodiments, regimen 30 includes several different types of fully contracted exercises. In some embodiments, exercisers 10 initially engage in less complex fully contracted exercises, and then more demanding multi-fully contracted exercises as the exercise regimen progresses, as their disease or medical condition may dictate.

In some embodiments, the fully contracted exercises work all major muscle groups thereby achieving a full body workout. In some embodiments, exercisers 10 perform four fully contracted exercises: bench presses, leg presses, core pulls, and vertical lifts as seen in FIG. 3. In each of these fully contracted exercises, the relevant muscle groups are maintained in the fully contracted state while creating increasing amounts of force until muscle failure is achieved. In some cases, all of these exercises are performed on solid-state exercise equipment 40 designed specifically to allow the exerciser to fully contract the relevant muscle groups while creating increasing amounts of force with the fully contracted muscle groups.

A description of fully contracted exercises in accordance with some embodiments of the present disclosure will now be described. A goal of each of these fully contracted exercises is to achieve the maximum level of muscle fiber involvement. Without intending to be limited to any particular theory, the fully contracted exercises are based on the observations that (i) muscle fibers contract by reducing their length; (ii) a muscle is in the fully contracted (peak position) when all the fibers of the muscle are contracted simultaneously; and (iii) to get all the fibers of a muscle to contract at the same time, a load intense enough to activate all of the muscle's fibers needs to be imposed. The four basic fully contracted exercises described here are improved versions of traditional compound, multi joint exercises.

Bench Press Fully Contracted Exercise.

The exerciser's proper position for the bench press fully contracted exercise requires the exerciser to be in a sitting position, with arms positioned in a horizontal plane passing through the shoulder joints, and holding about 2-3 inches short of where the arms are fully extended, the strongest part of the exercise. In this position, an exerciser can go to failure using one hundred percent of muscle fiber in the triceps, deltoids, and the pectorals. The exercise begins and ends in this position and there is only nominal movement due to compression of connective tissues within the body as well as the pad which sits behind the exerciser.

Leg Press Fully Contracted Exercise.

The exerciser's proper position for the leg press fully contracted exercise requires the exerciser to be seated upright and in no way semi supine. The exerciser is positioned in a seat with a high back and hand grips which is held to avoid riding up in the seat when performing the exercise. The upright positioning is dictated by the need to allow women in street clothes, who may possibly be wearing a skirt to avoid having her legs in an upright position at any time. When the exercise is performed the exerciser's legs are 4-6 inches from the position where the legs would otherwise be fully extended, the strongest part of the exercise. In this range an exerciser can go to failure using one hundred percent of muscle fiber in the quadriceps and the gluteus maxims. The exercise begins and ends in this position and there is only nominal movement due to compression of connective tissues within the body as well as the pad which sits behind the exerciser.

Core Pull Fully Contracted Exercise.

The exerciser's proper position for the core pull fully contracted exercise requires the exerciser to stand with legs close to the bar to be lifted. The bar is positioned 2-3 inches above the exerciser's knee. The exerciser performing the core pull fully contracted exercise must keep the bar almost touching the bottom of the rib cage as the exerciser is in a bent knee stance and has the upper body tilted forward at a 45 degree angle. In this range, an exerciser can go to failure using one hundred percent of muscle fiber in the biceps brachia, and the latissimus dorsi. The exercise begins and ends in this position and there is only nominal movement due to compression of connective tissues within the body.

Vertical Lift Fully Contracted Exercise.

The exerciser's proper position for the vertical lift fully contracted exercise requires the exerciser to stand close to the vertical lift bar, where the bar is located 2-3 inches above the exerciser's knee, and at the top most position where the bar is laying against the thighs and is being gripped so that the load is taken by a pulling motion as the center of gravity is close to the body, this results in the exerciser having proper balance and contraction of almost every muscle on the back side of the body. In this position, an exerciser can go to failure using one hundred percent of the muscle fiber in the hamstrings, spinal erectors, trapezius, abdominals, calves, and forearms. The exercise begins and ends in this position and there is only nominal movement due to compression of connective tissues within the body.

In some embodiments, exercisers 10 use their muscles to create a force resisted and measured by equipment 40. In some embodiments, strain gauges on exercise equipment 40 are utilized to measure the amount of force used in the fully contracted exercise. In other embodiments, the strain gauges monitor the amount of force exerciser 10 is voluntarily creating. In some instances, exerciser 10 creates pressure while they are sitting or standing.

In some embodiments, exerciser 10 creates the increasing force as long as possible. The exerciser 10 releases equipment 40 when the exerciser's targeted muscle groups cannot withstand the pressure any longer. In some embodiments, after the exerciser 10 releases equipment 40, the computer systems and software are designed to measure the maximum force the exerciser 10 was able to create. The maximum force is an example of one form of "exercise result" in accordance with the present disclosure. In other embodiments, the number of repetitions the exerciser completes is an exercise result. In still other embodiments, the length of time that the exerciser created the force is an exercise result.

In some embodiments, exerciser 10 can view graphical displays of exercise results both during the exercise appointment and/or any time after the exercise appointment via the enterprise website 78 (FIG. 5). In some embodiments, this information is also be available on a display 45 that is attached to exercise equipment 40 as illustrated in FIG. 3. In addition, in some embodiments, each exerciser may visually see the incremental progress made on an appointment by appointment basis 61, and/or the progress made against long term goal elements 62 (FIG. 4). In some instances, the exerciser's exercise results are transferred via a network in an encrypted manner to a central data processing system 70. In one embodiment, exercisers 10 initially build strength at a rapid rate, but then their strength gains are slowed down due to physical limitations which could include, but are not limited to, lack of progress in their bench press exercise progress or inability for their hands to handle the load that is put upon them. In such embodiments, the intensity of the exercise regimen 30 is slightly decreased. The intensity of the program is restored by concurrently (i) increasing the number of consecutive contractions and (ii) decreasing the amount of time allotted to complete such contractions. In some embodiments, an exerciser's regimen 30 is determined by first calculating a force number that is below their maximum fully contracted load/force. Then a determination is made as to how many times they can hit that load/force number. As the client progresses, higher contraction numbers are chosen and progress is monitored by looking at how many contractions can be achieved with the intended force in the shortest time. These values are then compared to previous performances with the same force applied. Progress in such an embodiment is graphically illustrated in FIG. 4 as graph 62.

Advantageously, exerciser 10 does not need to change clothing to perform the exercises, and may in fact perform them in any clothing. In some embodiments, exercisers 10 can arrive comfortably in their street clothing, and leave a few minutes later looking like they did when they arrived for their appointment. In some embodiments, a complete exercise appointment lasts twenty minutes or less, fifteen minutes or less, ten minutes or less, or even five minutes or less. After completing an exercise regimen 30, the exerciser 10 waits a specified amount of time, which allows the body to recover and then develop additional skeletal muscle, before completing another exercise regimen 30. This period of time where the exerciser performs no fully contracted exercises is referred herein as the "recovery period" 63 (also referred to herein as the "recovery cycle"). In some embodiments, the exerciser 10 receives a hard copy print-out of the appropriate recovery period 63 or may access the recovery period 63 via the Internet. In some embodiments, this information may also be available on display 45 located on the exercise equipment 40 (FIG. 3).

In some embodiments, the recovery period is calculated based on previous exercise results and the exerciser's pre-screening medical information. In some embodiments, the recovery period is a function of an exerciser's exercise result and the results or experience trends of other exercisers that use the disclosed fully contracted exercise regimen. In some instances, these other exercisers share one or more characteristics in common with the exerciser 10. Such characteristics may include health conditions, age, or gender.

Once the recovery period 63 is complete, the exerciser 10 returns to the equipment 40 to perform another set of exercises in the presence of a fitness trainer. Such activity is referred to as a "subsequent exercise appointment." In some embodiments, the type of exercises, the repetitions, the exerciser created force, or other variables are different in subsequent exercise appointments.

In some embodiments, data analysis 73 is performed once system 70 receives two or more exercise results. In some instances, the force created for any given exercise across multiple exercise appointments is evaluated together in order to determined changes in performance. As an example, the force created in a specific exercise type during one exercise appointment can be compared to the force created in an exercise of the same exercise type during another exercise appointment and the two results can be evaluated together for performance changes. In some embodiments, the results of the data analysis 73 are combined with any exercise constraints set by a physician in order to dictate changes in the exerciser's program details. Such changes include, but are not limited to, recovery period length 63, the amount of force created, the number of exercise repetitions, the type of exercises performed, the instantaneous load/force limit, the static load/force limit, and total exertion intensity.

In some embodiments, when an exerciser's incremental progress begins to slow, possibly from overtraining, more time can be added to the recovery period 63. In such instances, for example, exercise appointments can be scheduled every other week. In some embodiments, a lower demand is placed on the connective tissue but a similar type of momentary muscular failure is still achieved, and the exerciser 10 is able to continue their strength development. Furthermore, when an exerciser 10 begins to near their muscular genetic potential, meaning that they have developed muscles worked by the disclosed exercise regimens to their fullest possible extent, maintenance of such a condition can require as little time as one to two appointments per month. As a result, some embodiments of the present invention are capable of meeting the needs of exercisers 10, in part because they will have gradually increasing long term goals that they can work toward and met over an extended period of time.

In some embodiments, a central data processing system 70, also referred to as a "central system," is provided in order to assists in the administration of the disclosed exercise programs. Aspects of a central system in accordance with the present disclosure are illustrated in FIGS. 4 and 5.

In some embodiments, this central system assures one or more of the following: the privacy needed for medical information, a totally disciplined structure for all types of information collection, a consistent manner in which prescreening medical information is collected by appointment, and the general administration of the business, including, all reporting, accounting and electronic billing 75. In other embodiments, the central system 70 receives its data from a plurality of sites via a network 50 and subsequently processes, distributes, and stores, encrypted db files 71 and extracted database files 72 for future access and segmentation analysis.

In some embodiments, the disclosed communications control, application programs, database management system, and operating system data management reside within central system 70. Together these elements protect, process, store and distribute the information necessary for the operation of the exercise program.

In some embodiments, a plurality of exercise training sites can transmit exercisers' medical information and exercise data, including but not limited to exercise results, constraints, or goal elements, to a central data processing facility utilizing a Network/Internet/Intranet or wireless connection 50 while maintaining the privacy of each exerciser's confidential data in the process. In some embodiments, this data is encrypted while being transferred.

In some embodiments, exerciser specific analysis 73 is performed when this data reaches central data processing system 70. In other embodiments, this analysis 73 utilizes interactions between databases, proprietary algorithms, and standard statistical techniques commonly used in the medical industry. In addition, in some embodiments, the resulting output information includes exerciser progress by appointment 61, long term goal achievement 62, and next recovery period 63 instructions. In the present disclosure, the prescribed recovery period 63 dictates the amount of time before an exerciser can have his or her next exercise appointment.

The ability to transmit data from a plurality of sites via a network 50 may also allow the processing and storage of exercise data for each individual exerciser 10. In some embodiments, this data is processed and stored for each exercise an exerciser 10 performs during a training session. Furthermore, the embodiments having accurate and reproducible data collection methods are able to make and store reliable accurate data calculations. In some embodiments, the results of these data calculations 61, 62, and 63 are displayed so that each exerciser 10 can graphically see their own progress.

In some embodiments, both personal trainers and other interested parties are provided an exerciser's specific data and progress information. In addition, some embodiments also provide real time support for personal trainers. In some instances, the automation and centralization of data processing in the central server 70 precludes personal trainers from changing any data. In some embodiments, the central server's central processing functions assure that personal trainers are fully supported by software driven help functions that permit them to address any exercisers 10 needs correctly and consistently from a plurality of personal trainers, located across a distributed network.

In some embodiments, the central system 70 also performs the necessary accounting and billing 75, as well as processes the broad array of information needed to properly administer 76 the enterprise. Some embodiments will also interact electronically with physicians, employers of exercisers, and in certain cases the insurance carriers 77 of exercisers. In some instances, the enterprise management team is provided both general and medically specific information 74 supporting the continual improvement of the exercise program and data collection techniques and strategies.

In some embodiments of the present disclosure, the centralized automated processing of information, privacy control, medical risk management, and solid state equipment 40 design are treated as one integrated administrative system 60, 70. Furthermore, in some embodiments, the exerciser is largely oblivious to the central system that supports the plurality of solid state machines 40 and the fitness trainers that comprise this exercise program. In such embodiments, the exerciser 10 only sees personal exercise results that are displayed on the electronic display located on the equipment 40.

FIGS. 6A-6J illustrates the results for ten different exercisers that have used the disclosed systems and methods. For each exerciser, the amount of force the exerciser was able to apply in each of four different fully contracted exercises (bench press, leg press, core pull, and vertical lift) during specific exercise sessions is graphically displayed. Furthermore, the recommended amount of recovery time (e.g., less than a week of rest, 1 week of rest, 2 weeks of rest, 3, weeks of rest, 4 weeks of rest) between exercise sessions is given. Further, forward-looking advice computed using the algorithms of the present disclosure are provided. Details of one such algorithm are provided below.

Exemplary Algorithm for Computing Recovery Time and Forward Looking Advise.

The exemplary algorithm described here is a compendium of discreet elements (feedback options) to aid the exerciser. These feedback options are displayed on the exerciser's print-out of exercise results (e.g., FIGS. 6A-6J) and/or on their log in screen. The user's exercise data is analyzed to dictate which feedback option is appropriate. Data considered to select a specific feedback option is (i) the results of last results from the bench press (B), leg press (L), vertical lift (D), and bench row (R) fully contracted exercises and (ii) whether progress was made or not in these specific four exercises in terms of the amount of force exerted. In the tables below, "x" means that progress has been made in a particular fully contracted exercise during the last exercise session relative to the exercise session just prior to the last exercise session. Further, "o" indicates that no progress has been made in a particular fully contracted exercise in the last exercise session relative to the exercise session just prior to the last exercise session.

| Feedback option No. 1. | | | |
|---|---|---|---|
| B | L | D | R |
| x | x | x | X |

The message to the exerciser is: "[y]ou are making great progress in all exercises, this indicates that the time between repeating the same exercise and the time for your entire system to recover and finish tissue fortification is at the proper level. Please note that progress like this may continue for weeks, or possibly progress will slow down. Assuming that there is a slow down in your near future, it only means that you are building muscle and the larger muscles need a longer period of time to recover."

The suggestion to the exerciser is to stay on the current recovery schedule.

| Feedback option No. 2. | | | |
|---|---|---|---|
| B | L | D | R |
| o | x | x | X |

The message to the exerciser is: "[y]ou are making progress in all exercises with the exception of the Bench Press. This could simply mean for one reason or another you had less than perfect form in the exercise, possibly you did some exhausting activity with the Bench Press target muscle groups which would pre-exhaust you, or even that your mind may have not been as focused on the task at hand as in previous exercise sessions. No matter the reason for this lack of progress, as it is only one out of the four, and it is likely an anomaly which doesn't necessarily indicate overtraining."

The suggestion to the exerciser is to stay on current recovery schedule.

| Feedback option No. 3. | | | |
|---|---|---|---|
| B | L | D | R |
| x | o | x | X |

The message to the exerciser is: "[y]ou are making progress in all exercises with the exception of the Leg Press. This could simply mean for one reason or another you had less than perfect form in the exercise, possibly you did some exhausting activity with the Leg Press target muscle groups which would pre-exhaust you, or even that your mind may have not been as focused on the task at hand as in previous exercise sessions. No matter the reason for this lack of progress, as it is only one out of the four exercises, and is likely an anomaly, which doesn't necessarily indicate overtraining"

The suggestion to the exerciser is to stay on current recovery schedule.

| Feedback option No. 4. | | | |
|---|---|---|---|
| B | L | D | R |
| x | x | o | X |

The message to the exerciser is: "[y]ou are making progress in all exercises with the exception of the Vertical lift. This could simply mean for one reason or another you had less than perfect form in the exercise, possibly you did some exhausting activity with the Vertical lift target muscle groups which would pre-exhaust you, or even that your mind may have not been as focused on the task at hand as in previous exercise sessions. No matter the reason for this lack of progress, as it is only one out of the four exercises, and is likely an anomaly, which doesn't necessarily indicate overtraining"

The suggestion to the exerciser is to stay on current recovery schedule.

| Feedback option No. 5. | | | |
|---|---|---|---|
| B | L | D | R |
| x | x | x | O |

The message to the exerciser is: "[y]ou are making progress in all exercises with the exception of the Core pull. This could simply mean for one reason or another you had less than perfect form in the exercise, possibly you did some exhausting activity with the Core pull target muscle groups which would pre-exhaust you, or even that your mind may have not been as focused on the task at hand as in previous exercise sessions. No matter the reason for this lack of progress, as it is only one out of the four exercises, and is likely an anomaly, which doesn't necessarily indicate overtraining."

The suggestion to the exerciser is to stay on current recovery schedule.

| Feedback option No. 6. | | | |
|---|---|---|---|
| B | L | D | R |
| o | o | x | X |

The message to the exerciser is: "[y]ou are making progress in all of your pulling exercises, however your Pushing exercises are lagging. This could mean a few things, but the highest probability is that you were just having an off day. It is unlikely that this would indicate overtraining as the pulling exercises are progressing, and more importantly the muscle groups used in the leg press are the largest ones in the body they are usually the last ones to show resource overtraining"

The suggestion to the exerciser is to stay on current recovery schedule.

| Feedback option No. 7. | | | |
|---|---|---|---|
| B | L | D | R |
| o | x | o | X |

The message to the exerciser is: "[y]ou are making progress in the Leg Press and in the Row, however no progress in the Bench Press and the Vertical lift. The most likely explanation for this is either multiple location specific issues, as in a sore shoulder and a pain in the lower back. This pattern is both unlikely and not indicative of overtraining Your advisor should take note of this lack or progress and take special care to observe your exercise form."

The suggestion to the exerciser is to stay on current recovery schedule.

| Feedback option No. 8. | | | |
|---|---|---|---|
| B | L | D | R |
| o | x | x | O |

The message to the exerciser is: "[y]ou are making progress in the Leg Press and in the Vertical lift, however no progress in the Bench Press and the Row. This could be an indication of localized overtraining. Both the Bench Press and the Row use much smaller muscle groups than the Vertical lift and Leg Press do. Therefore you may be doing something in everyday life that is exhausting your upper-body and thereby halting potential development. Unless you feel that this is an anomaly caused by poor form or a lack of focus it is advisable that you take more time to recover between exercise sessions."

The suggestion to the exerciser is to add extra recovery time into the exercise schedule.

| Feedback option No. 9. | | | |
|---|---|---|---|
| B | L | D | R |
| x | o | o | X |

The message to the exerciser is: "[y]ou are making progress in the Bench Press and in the Row, however no progress in the Leg Press and the Vertical lift. This isn't necessarily a common situation due to the Leg Press and Vertical lift utilizing larger muscle groups, they are usually the last groups to indicate overtraining. This situation doesn't indicate overtraining and could possibly indicate a back soreness or injury. If this trend continues it would be advisable to look at some of the activities that you partake in during an average week that could be exhausting your lower body."

The suggestion to the exerciser is to stay on current recovery schedule.

| Feedback option No. 10. | | | |
|---|---|---|---|
| B | L | D | R |
| x | o | x | O |

The message to the exerciser is: "[y]ou are making progress in the Bench Press and in the Vertical lift, however no progress in the Leg Press and the Row. This isn't necessarily a common situation and it is not possible that these two things are connected. It is possible that your general energy level is down and you are not in the best frame of mind when exercising. This situation doesn't look to be overtraining and you should maintain your present schedule of exercise."

The suggestion to the exerciser is to stay on current recovery schedule.

| Feedback option No. 11. | | | |
|---|---|---|---|
| B | L | D | R |
| x | x | o | O |

The message to the exerciser is: "[y]ou are making progress in all of your Push exercises, however your Pull exercises are lagging. This could mean a few things, but the highest probability is that you were just having an off day. It is unlikely that this would indicate overtraining as the pulling exercises are progressing, and more importantly the muscle groups used in the leg press are the largest ones in the body they are usually the last ones to show resource overtraining"

The suggestion to the exerciser is to stay on current recovery schedule.

| Feedback option No. 12. | | | |
|---|---|---|---|
| B | L | D | R |
| x | o | o | O |

The message to the exerciser is: "[y]ou are only making progress in the Bench Press. This could indicate getting over an illness or possibly a general lack of energy for one reason or another, however this most likely means that you are overtraining. It would be advisable that you add more time between your exercise sessions. This will give you more time to recover, and enable you to make progress once both initial recovery and tissue fortification have taken place."

The suggestion to the exerciser is to add extra recovery time into the exercise schedule.

| Feedback option No. 13. | | | |
|---|---|---|---|
| B | L | D | R |
| o | x | o | O |

The message to the exerciser is: "[y]ou are only making progress in the Leg Press. This could indicate getting over an illness or possibly a general lack of energy for one reason or another, however this most likely means that you are overtraining. It would be advisable that you add more time between your exercise sessions. This will give you more time to recover, and enable you to make progress once both initial recovery and tissue fortification have taken place."

The suggestion to the exerciser is to add extra recovery time into the exercise schedule.

| Feedback option No. 14. | | | |
|---|---|---|---|
| B | L | D | R |
| o | o | x | O |

The message to the exerciser is: "[y]ou are only making progress in the Vertical lift. This could indicate getting over an illness or possibly a general lack of energy for one reason or another, however this most likely means that you are overtraining. It would be advisable that you add more time between your exercise sessions. This will give you more time to recover, and enable you to make progress once both initial recovery and tissue fortification have taken place."

The suggestion to the exerciser is to add extra recovery time into the exercise schedule.

| Feedback option No. 15. | | | |
|---|---|---|---|
| B | L | D | R |
| o | o | o | X |

The message to the exerciser is: "[y]ou are only making progress in the Row. This could indicate getting over an illness or possibly a general lack of energy for one reason or another, however this most likely means that you are overtraining. It would be advisable that you add more time between your exercise sessions. This will give you more time to recover, and enable you to make progress once both initial recovery and tissue fortification have taken place."

The suggestion to the exerciser is to add extra recovery time into the exercise schedule.

| Feedback option No. 16. | | | |
|---|---|---|---|
| B | L | D | R |
| o | o | o | O |

The message to the exerciser is: "[y]ou are not making progress in any of the exercises. This is usually simply an indication of overtraining, all that is necessary is to allow for both the entire body system and the specific muscles longer to go through the initial recovers, then through the tissue fortification phase."

The suggestion to the exerciser is to add extra recovery time into the exercise schedule.

When an exerciser takes a week off that isn't necessarily scheduled, or adds a week of rest time in between workouts, the analysis of the first time exercising after the break must only look at the current session in comparison to what was done in the session before where the same exercises were performed. For example, if an exerciser is on the split program where the exerciser does the Push exercises one week, then the Pull the following week, and then takes a vacation and skips a week, analysis of exercises that took place before the vacation would ignore the excess recovery variable, and hence should not be considered.

| After extra recovery time, option No. 1. | | | |
|---|---|---|---|
| B | L | D | R |
| — | — | x | X |

The message to the exerciser is: "[y]ou are making progress in both the Vertical lift and in the Row. As the recovery variables have changed since your last Push session there is no need to analyze those results."

The suggestion to the exerciser is to stay on current recovery schedule.

| After extra recovery time, option No. 2. | | | |
|---|---|---|---|
| B | L | D | R |
| — | — | o | X |

The message to the exerciser is: "[y]ou are making progress in the Row, however not in the Vertical lift. This most likely means you have some injury that possibly you aren't completely aware of. This would indicate that you are compensating while you are doing the Vertical lift and that is keeping you from taking the exercise to failure. The Vertical lift must be paid close attention to the next time you do it to take special note of your exercise form. As the recovery variables have changed since your last Push session there is no need to analyze those results."

The suggestion to the exerciser is to stay on current recovery schedule.

| After extra recovery time, option No. 3. | | | |
|---|---|---|---|
| B | L | D | R |
| — | — | o | O |

The message to the exerciser is: "[y]ou did not make progress in your Pull exercises. As you have just had extra recovery time overtraining is not likely, however IS a possibility. It is recommended that you continue on your prescribed schedule unless this lack of progress continues to your next session. In that case a clear indication of overtraining will be made and you must add more time between exercise sessions. As the recovery variables have changed since your last Push session there is no need to analyze those results."

The suggestion to the exerciser is to stay on current recovery schedule.

| After extra recovery time, option No. 4. | | | |
|---|---|---|---|
| B | L | D | R |
| x | x | — | — |

The message to the exerciser is: "[y]ou are making progress in both the Bench Press and in the Leg Press. As the recovery variables have changed since your last Pull session there is no need to analyze those results."

The suggestion to the exerciser is to stay on current recovery schedule.

| After extra recovery time, option No. 5. | | | |
|---|---|---|---|
| B | L | D | R |
| o | x | — | — |

The message to the exerciser is: "[y]ou are making progress in the Bench Press, however not in the Leg Press. This most likely means you have some injury that possibly you aren't completely aware of. This would indicate that you are compensating while you are doing the Bench Press and that is keeping you from taking the exercise to failure. The Bench Press must be paid close attention to the next time you do it to take special note of your exercise form. As the recovery variables have changed since your last Pull session there is no need to analyze those results."

The suggestion to the exerciser is to stay on current recovery schedule.

| After extra recovery time, option No. 6. | | | |
|---|---|---|---|
| B | L | D | R |
| o | o | — | — |

The message to the exerciser is: "[y]ou did not make progress in your Push exercises. As you have just had extra recovery time overtraining is not likely, however IS a possibility. It is recommended that you continue on your prescribed schedule unless this lack of progress continues to your next session. In that case a clear indication of overtraining will be made and you must add more time between exercise sessions. As the recovery variables have changed since your last Pull session there is no need to analyze those results."

The suggestion to the exerciser is to stay on current recovery schedule.

Additional Exemplary Embodiments

Embodiments of the present disclosure involving an automated health risk managed system for physical development, also referred to as an "exercise program and administrative system," have been described above. What follows is more description of such systems and methods as well as optional embodiments encompassing the same.

In general, the systems and methods of the present disclosure employ a science based, solid state, data driven physical development technology program that provides interested parties, referred by physicians, and others, in selected locations, a novel and inherently safer method of fitness and strength training/testing. Primary health risk factors are used to screen for unacceptable injury risk, both initially and on an ongoing basis. For those exercisers that satisfy these pre-screen tests, highly accurate and repeatable strength test results are derived in a private setting with a personal trainer. Such results are transmitted, preferably in an encrypted manner, and analyzed by a central processor. Such analysis allows for a scientifically based incremental development program maximizing the balance between sufficient muscle stress for stimulating muscle development/strength and the optimal muscle tissue recovery time period needed between ongoing fully contracted training sessions.

The present disclosure provides an exceedingly safe, life long, health fitness and strength building exercise system. In some embodiments of the disclosure, there is an enterprise wide system of custom designed fitness equipment and custom designed software. The equipment is of a solid state design, with no moving parts, virtually eliminating traditional fitness equipment related exerciser injuries. The centralized software utilizes highly accurate medical information and highly accurate fitness equipment data collected from each exerciser, to analyze, plan, manage, and report to each exerciser their progress against pre-stated goals, thereby maintaining their interest and life long commitment to better health through improved strength and fitness.

In some embodiments, the present disclosure provides a closed loop, fully integrated, and complete health and fitness solution including an exercise program and administrative system to support a medical science based injury avoidance and long term strength building enterprise. In some instances, this embodiment provides a model by which high levels of equipment utilization, limited floor space, and a highly distributed system effectively reach larger populations of maturing adults. It also may have a highly structured data collection and processing capability, allowing more and more science based analysis of trends among larger and larger populations of exercisers, consistently resulting in improved analysis at the individual exerciser level.

Some embodiments of the present disclosure provide servers that mirror other servers, thereby protecting all enterprise data in a manner that could not be achieved economically without the plurality of sites connecting via a network to a central data center. Some embodiments of the present disclosure also provide a health science based service that can be supported by employers and insurance carriers as part of their commitment to improved preventative medical care for a maturing population.

Another aspect of the present disclosure is its family of solid state fitness machines that constitute a training/testing sub-system, utilizing non injury designs, and strain gauges for force measuring and data collection, combined with a personal trainer in a private setting, providing the proper medical focus on all aspects of the present invention. In some instances, the data collection is highly accurate and highly reproducible, allowing precise analysis and reporting of incremental progress, providing long term progress reporting against specifically stated goals, and permitting modulation of each exercisers recovery process.

In addition, some embodiments of the present disclosure include custom built exercise machines, employing no moving components during the time user loads are applied, thereby eliminating equipment failures that often result when traditional fitness equipment is utilized in typical fitness centers. In some cases, the present disclosure may also have enclosed adjusting mechanisms to accommodate differing anatomical characteristics of exercisers without allowing exercisers any access to adjusting mechanisms and thereby avoiding injury. In some instances, the adjusting mechanisms may have been load tested and calibrated to automatically compensate for every exerciser's anatomical differences, such that the performance parameters measured remain accurate, allowing scientifically accepted practices to be employed in the analyses performed for each exerciser, and the utilization of all data from the plurality of exercisers to be used in broad based group/type analysis. The present disclosure may also have a simple equipment design that precludes an exerciser from making an error resulting in injury. The invention may also only have concentric fully contracted loading that thereby eliminates eccentric contraction and associated injuries.

In some cases, the present disclosed solid state design eliminates the potential for stored energy so that the exerciser can only experience loads or forces that they alone apply with that energy immediately and completely dissipating once the voluntary contraction ceases. In other instances, the solid state design does not permit any load to be applied to an exerciser that the exerciser cannot handle, because the load/force applied is applied by the exerciser.

Some embodiments of the present disclosure provide a plurality of solid state machines, all of which are new in design concept, and utilize highly accurate training/testing measuring technology, not associated with traditional workout equipment. It may also include highly accurate load cells to measure exerciser applied forces, times, and cycles, resulting in accurate data from a plurality of exercisers to be processed for further use in adjusting an exercisers fitness program and prescribed recovery schedule.

Some embodiments of the present disclosure provide customized exerciser programs to meet physician objectives, as well as exerciser goals. In some instances, the invention also has the ability to eliminate a full range of motion and the injuries that typically result from traditional full range of motion fitness equipment. The equipment may also have the capacity to work all major muscle groups and thereby accomplish a full body workout bring the major muscle groups to failure.

In some embodiments, encrypted medical data, exercise data, and administrative information necessary to support the exercise program is communicated via a network. Some embodiments also include the consistent application of equipment and technology among a plurality of sites thereby allowing any individual exerciser to utilize any machine at any location and generate training/testing results that are equipment and site independent, thus permitting individuals to engage in the program irrespective of where they may be located at any particular time.

Another aspect of the present disclosure is the automated and centralized enterprise wide processing center system, also referred to herein as the "central system", that provides privacy for exerciser medical information, disciplined analysis of exercise data, and accurate reporting to each exerciser of progress in the program, while at the same time allowing for an information management system providing all information and data services required for the efficient and successful operation of the enterprise.

In some instances, the central system has the feature of receiving via a network all of the encrypted medical data, exercise data, and administrative information necessary to support the disclosed methods. It may also have the capacity to store encrypted medical files as well as extracted files and to interface with the operating system data management to support processing and reporting. The central system may also include an electronic prescreening feature as one element of the user interface for every exerciser appointment, further assuring that an exerciser cannot proceed without meeting certain designated health preconditions. Furthermore, the central system may also have the capacity to process exerciser health information, and training/testing data creating an exerciser specific fitness program, providing exerciser reports used to define safety constraints and goals for future exercise and recovery.

In addition, in some embodiments, the central system has the critical capability of calculating the prescribed recovery period for each separate exerciser, based on personalized data balanced against experience trends measured among other exercisers with various similar characteristics, such as health conditions, age, and gender among many characteristics. Moreover, the central system may also have the capacity, based on data base information, displayed on a user interface, to provide each exerciser with comments, on incremental fitness progress, as well as against long term goals. In some cases, the central server can also generate graphical displays showing incremental, and long term progress in terms that are understandable and comparable over years of strength building and strength maintenance.

Another feature of the central system is the capacity of providing to a plurality of sites, and designated centralized locations, the enterprise wide management information required for efficient operation, and compliance with standard medical practices, and laws affecting the business operations. In some cases, the present invention also includes interactive electronic information tools available at a plurality of sites as well as designated centralized business functions, the administrative information essential to operating an enterprise with centralized processing and distributed operations.

Yet another feature of the central system is the presence of a network of sites connected to a server based family of computer programs that avoid the unreasonable maintenance burden that would exist if a plurality of sites were required to install and maintain operational programs locally. In some cases the plurality of sites may be able to access the centralized support services for updates, and operations changes via a browser.

Another aspect of the central server is its ability to utilize the highly accurate strain gauge measurement data to calculate accurate results with precision. In addition, the central server may also be able to monitor participation in and compliance with a prescribed (by a physician) and/or paid for program of exercise (by an employer or other interested party) thereby providing accurate and ongoing feedback to those interested parties responsible for the physical and/or financial support of the exerciser.

In some embodiments, the central server may also include the necessary accounting and billing functions required for billing employers, insurance carriers, individual exercisers, and other parties. In some instances, the central server will also have the necessary functional interfaces to support automatic credit card debiting and Automated Clearing House (ACH) electronic funds transfers to facilitate all billing of exercisers for services and goods, eliminating the need for any personal trainer and his/her exerciser to become involved personally in any financial transactions at a plurality of sites. The central server may also include additional financial functions necessary for full support of accounting, enterprise finance, regulatory compliance and general enterprise administration.

In some embodiments, the central server health information collection sub-system that prescreens each exerciser before any exercises are performed, to determine the exerciser's suitability for the program and to provide specific constraints that any particular exerciser may require to maintain safety. In some instances, the automated central system provides privacy for medical data, and access for incremental exerciser data, to support the processing and reporting of progress against goals, and prescribed recovery.

In some instances, medical criteria also determine, define, and/or constrain the appointment by appointment exercise regimens in the present invention and prescribe the appropriate recovery period for each individual exerciser. In some examples, the exercise regimen is unique to the exerciser and not selected from a family of standard programs. The present invention may also have an online video support feature in the form of help, and training/testing results, for both the exerciser and the personal trainer assisting the exerciser.

The present disclosure also includes services offered to physicians and their patients, to specifically define pre-operative strength building programs as an aid to facilitating post operative recovery. In other embodiments, the present disclosure includes services that set long-term exerciser goals that can be met over a period of years, thereby avoiding the exceedingly short-term commitments exercisers have demonstrated when using traditional fitness industry equipment, facilities, and programs.

The present disclosure can be implemented as a computer program product that comprises a computer program mechanism embedded in a tangible computer readable storage medium. For instance, the computer program product could contain the program modules of FIG. 5. These program modules can be stored in a CD-ROM, DVD, magnetic disk storage product, or any other tangible computer readable data or program storage product.

Exemplary Diseases and Conditions Addressed by the Disclosed Apparatus and Methods The disclosed apparatus and methods promotes, provides, supports and solves many of the medical needs already clearly documented in clinical studies and existing medical practice. Disclosed herein are exemplary diseases and medical conditions that are effectively addressed by the disclosed apparatus and methods.

The disclosed apparatus and methods help to build muscle which improves insulin sensitivity and increases metabolism/calorie burning, and helps to decrease visceral fat. As such, the disclosed apparatus and methods address is an effective treatment for metabolic syndrome. The disclosed apparatus and methods are appropriate for various disease states to improve exercise tolerance and shortness of breath. As such, the disclosed apparatus and methods are appropriate for deconditioned states arising from, for example, muscle atrophy and cardio weakness. The apparatus and methods of the present disclosure provide maximum load or weight bearing exercise on the body as recommended by the United States Surgeon General to improve bone density. As such, the apparatus and methods of the present disclosure are suitable for treating the symptoms of osteoporosis and osteopenia. The disclosed apparatus and methods improve core strength, balance, and agility and thus are appropriate to treating subjects that are at risk for falling or otherwise susceptible to injury, including the elderly and disabled. The disclosed apparatus and methods improve insulin sensitivity by improving physical fitness and stamina. Using the disclosed apparatus and methods results in a decline in blood glucose levels. Thus, the disclosed apparatus and methods are suitable for subjects that have diabetes.

Many post-surgical activities need medical clearance by the surgeon or care-giving physician. However, as the loading is self imposed with the disclosed apparatus and methods, an individual has the ability to self regulate just how much stimulus is possible. As such, the disclosed apparatus and methods are suitable for post-surgical orthopedic conditioning/strengthening.

The disclosed apparatus and methods improve strength, proprioception, and posture leading to decreased pain. As such, the disclosed apparatus and methods are suitable for non-specific chronic lower back pain.

The disclosed apparatus and methods help to stimulate mechano-receptors and desensitize pain receptors, improves production of testosterone, human growth hormone, and serotonin. Moreover, training using the disclosed apparatus and methods decrease stiffness and improves mobility. As such the disclosed apparatus and methods are suitable for the treatment of fibromyaligia.

The disclosed apparatus and methods provide training that boosts metabolism and builds muscle mass, which can contribute to weight reduction. As such, the disclosed apparatus and methods are suitable for addressing obesity.

The disclosed apparatus and methods improve strength, stability, coordination, and balance. Training using the disclosed apparatus and methods helps flexibility, reduces muscular atrophy, and helps prevent falls. As such, the disclosed apparatus and methods are suitable for treatment of Parkinson's disease and multiple sclerosis.

Through the maintenance of muscle mass using the apparatus and methods of the present disclosure, atrophy is avoided or minimized and the activities of daily living are preserved throughout life. As such, the apparatus and methods of the present disclosure are suitable for maintenance of activities of daily living.

Weakened lower back muscles are often the cause of pain. These muscles can be easily strengthened using the apparatus and methods of the present disclosure, and done in a low risk way. Lower back pain has been found to decrease substantially or disappear completely using the apparatus and methods of the present disclosure.

Athletes often have to deal with injuries picked up in training and competition, or with lower backaches and strains caused through excessive stress on the body. Using the apparatus and methods of the present disclosure, these complaints can be treated quickly and efficiently and the body's own healing process can be greatly assisted. Athletes have found the apparatus and methods of the present disclosure to be indispensable for rehabilitation. The ability to strengthen muscles without strain on joints and ligaments assists those with rehabilitation needs. Increased blood circulation helps bring oxygen to inflamed areas to promote healing, while improved lymphatic flow helps drain fluid build-up from injured tissue. As such, the apparatus and methods of the present disclosure are suitable for addressing sports injuries.

Mental health disorders such as depression and anxiety affect millions of people worldwide and are associated with increased morbidity and healthcare costs. Physical activity has a positive impact on mental health and psychological well-being. The ease with which individuals can access and utilize the apparatus and methods of the present disclosure makes it exceedingly helpful in treating mental health.

Although resistance training has long been accepted as a means for developing and maintaining muscular strength, endurance, power and muscle mass (hypertrophy), its beneficial relationship to health factors and chronic disease has been recognized only recently. Prior to 1990, resistance training was not a part of the recommended guidelines for exercise training and rehabilitation for either the American Heart Association or the American College of Sports Medicine (ACSM). In 1990, the ACSM first recognized resistance training as a significant component of a comprehensive fitness program for healthy adults of all ages. Isometric exertion involves sustained muscle contraction against an immovable load or resistance with no change in length of the involved muscle group or joint motion. The heart rate and blood pressure responses to isometric exertion are largely proportionate to the tension exerted relative to the greatest possible tension in the muscle group rather than the absolute tension developed. The result is a moderate increase in cardiac output, with little or no increase in metabolism. The combination of AHA and ACSM recognition of the benefits conferred on subjects by the apparatus and methods of the present disclosure along with improved strength and measurable results produces positive physiological benefits to users.

The apparatus and methods of the present disclosure are suitable for improving cardiovascular system health. There is a direct relation between physical inactivity and cardiovascular mortality, and physical inactivity is an independent risk factor for the development of coronary artery disease. The greatest potential for reduced mortality is in the sedentary who become moderately active. Because the level of fatigue (intensity) is an important factor for attaining optimal benefits, the regular use of the apparatus and methods of the present disclosure at volitional or near-volitional levels of fatigue is recommended to improve cardiovascular system health. The apparatus and methods of the present disclosure provide neurological benefits. Physical activity has been shown to be neuroprotective in many neurodegenerative and neuromuscular diseases. For instance, it reduces the risk of developing dementia. The disclosed apparatus and methods are provide benefits to the brain because the resultant exercises provide blood and oxygen flow to the brain, increasing growth factors that help create new nerve cells, and promote synaptic plasticity, increasing chemicals in the brain that help cognition, such as dopamine, glutamate, norepinephrine, and serotonin.

Exemplary Exercise Machine

FIGS. 7-9 show an exercise machine 101 that can be used with the system described above. The machine 101 enables a user to perform at least three types of exercises—chest press, core pull and leg press—while sitting, and a vertical lift exercise while standing. For this purpose, the machine 101 includes a sitting section 111 for the user to perform the sitting exercises, a standing section 112 for the user to perform the vertical lift exercise. The machine 101 further includes two displays 121, 122 that provide information to the user when the user is performing exercises respectively in the sitting and standing sections. An optional third display 123 displays information to an attendant that operates the exercise machine 101.

The user can be, for example, a patient having a disease for which a treatment entails the user exercising on the machine 101. The optional attendant is an operator of the machine 101, such as a health advisor, that monitors and controls the machine's operation and instructs the user on how to use the machine.

The machine sits on an imaginary longitudinal axis $A_L$. In the following description of the machine's components, "axial" refers to a direction parallel with the longitudinal axis, and "transverse" refers to a direction crossing or parallel to the longitudinal axis.

A base frame 130 of the machine 101 includes first and second parallel axially-opposite transversely-extending end beams 131, 132. The end beams 131, 132 are adjoined to axially opposite ends of two parallel axially-extending side beams 134. The frame 130 is supported above a floor by four feet 136. The feet 136 are adjustable to enable leveling the frame 130 and enable engagement of all four feet 136 on a nonplanar floor. The side beams 134 are attached to, and support, a horizontal non-skid first platform 138 that supports the user's feet when the user is in the sitting section 111.

The sitting section 111 includes a chair structure 140 with a cushioned seat 141 and a cushioned backrest 142. The backrest 142 includes a substantially-straight upper section 143, a concave middle section 144 and convex lower section 145 for lumbar support. An adjustable-length seat belt 146 extends from one side of the seat 141 to the transversely-opposite side of the side of the seat 141.

The chair structure 140 is slideably supported on a chair-support frame 150. The chair-support frame 150 has three parallel axially-extending rails, comprising two seat-bearing rails 151, 152 and a seat-stop rail 153 transversely-centered in-between. These rails 151-153 are located on a common plane, and are adjoined together by two axially-opposite transversely-extending end rails 154. The chair structure 140 slides axially forward and rearward ("forward" in the sitting section means in the direction that the backrest faces, and "rearward" means opposite that) over the seat-bearing rails 151, 152 by means of roller bearings (note shown). This sliding movement enables the chair structure 140 to be moved to any one of eleven seat positions spaced along the rails, corresponding to eleven holes 155 in the center rail 153. The chair structure 140 can be locked in place in any one of these positions by a latch device 156 that includes a lock/release lever 158. Pivoting the lever 158 in one direction causes a bolt in the latch device 156 to enter one of the eleven holes 155 in the seat-stop rail 153 to lock the chair structure 140 in place. Pivoting the lever 158 in the opposite direction withdraws the bolt 159 from the hole 155 to release the chair structure 140 to enable the chair structure 140 to slide along the seat-bearing rails 151, 152 to another position. The seat's position is defined by a position setting number based on which hole the bolt 159 is in. Seat position setting "1" corresponds to the rearmost hole, and "11" corresponds to the forward-most hole. The seat position setting will generally be inversely related to the height of the user.

A rear section of the chair-support frame 150 is connected to the base's first end beam 131 by a seat hinge 162. The seat hinge 162 includes a transversely-extending shaft 164, pivotably attached by a lower bracket 166 to the base frame 130 and by an upper bracket 168 to the chair-support frame 150.

The chair-support frame 150 is prevented from pivoting about the seat hinge 162 by a seat-support bar 170. This bar 170 extends upward from a lower bracket 171 attached to the first platform 138 to and to the seat-lock rail 153 at the front of the chair-support frame 150. Accordingly, downward gravitational force on the seat 141, by the weight of the user, applies compressive force to the seat-support bar 170. Conversely, upward force during the core pull exercise applies a tensile force to the seat-support bar 170, which counteracts the aforementioned compressive force. Since the seat-support bar 170 is sloped upwardly rearward and since the three chair-support rails are sloped rearwardly downward, rearward force on the seat and the backrest, produced during the chest press and leg press exercises, produces rearward torque 173 about the seat's hinge structure. This applies tensile force to the seat-support bar 170.

The resultant force on the seat-support bar 170, from the compressive load applied by the user's weight and from the tensile force applied by the user during exercises, are measured by a first force sensor 174 on the seat-support bar. This sensor 174 includes a load cell that converts the load on the seat-support bar to an analog signal, electronic circuitry that converts the analog signal to a USB-compatible digital signal, and a USB port that outputs the digital signal.

A retractable seat-supported foot rest 180 includes a horizontal transversely-extending foot-support bar 182 that is hingedly adjoined by a bracket 184 to the seat-lock rail 153. The foot rest 180 can be rotated forward and locked into a functional position for supporting a user's feet during the chest press exercise. And it can be rotated rearward into a retracted position out of the way of the user's feet during the other exercises. Since the foot rest 180 is suspended from the chair-support frame 150, when the user's feet rest on it, the weight of the user's legs is sensed by the first force sensor 174 along with the weight of the rest of the user's body.

Two seat-side handgrips 190 are fixed to laterally opposite sides of the seat and project in an upwardly forward direction. The distal ends of these handgrips 190 are below the top surface of the seat 141.

The standing section 112 includes a horizontal second platform 200 for the user to stand on while performing the vertical lift exercise. The second platform 200 is supported above the floor by its front end 202 ("front" relative to the orientation of the user when performing the vertical lift exercise) being attached to the second end beam 132 and by two adjustable-height feet 204 attached to its bottom surface.

A tower 210 is located axially between the sitting and standing sections 111, 112. The tower 210 includes two parallel transversely-opposite A-frames 212. Each A-frame 212 is attached to, and extends upward from, a respective side beam 134 of the base 130. The A-frames 212 are attached together at their tops by a cross-structure 213.

A leg press plate 214 is secured to both A-frames 212 in the sitting section. The foot plate 214 is inclined upwardly forward. The user's feet press against the leg press plate 214 in the leg press exercise.

An axially-extending load arm 220 includes two axially-extending side bars 222. The side bars 222 are adjoined at their axially opposite ends 224 to first and second transversely-extending cross bars 225, 226, located respectively in the sitting and standing sections 111, 112. The side bars 222 are rotatably joined to the tower 210 by a hinge 228 in the middle (which is not necessarily at the center) of the load arm 220, about which the load arm 220 pivots.

The load arm 220 supports three pairs of loading contact surfaces: A pair of chest-press loading contact surfaces 230 project transversely outward, in a downward angle, from the ends of the first cross bar 225 to enable natural positioning of the wrists. A transversely-extending core pull loading contact surfaces 240 are part of a single bent bar 242 that is attached, at its two distal ends 244, to the ends of the first end bar 225. The bent bar 242 has two side bar sections 246 that slope forwardly downward from the chest-press loading contact surfaces 230 to the first cross bar 225. This positions the core pull loading contact surfaces 240 above and rearward from the first cross bar 225. The core pull loading contact surfaces 240 are inclined to enable natural positioning of the wrists. In the standing section 112, a pair of vertical-lift loading contact surfaces 250 extend horizontally and transversely outward from opposite ends of the second cross bar 226. Each of the four pairs of loading contact surfaces 214, 230, 240, 250 are thus connected, indirectly, to the base 130 and supported by the base 130.

The vertical-lift loading contact surface 250 is axially spaced apart from each of the chest-press loading contact surface 230 and the core pull loading contact surface 240. When the user performs any one of the sitting or standing exercises, he/she faces axially toward all three of the chest-press, core pull and vertical-lift loading contact surfaces 230, 240, 250.

In the standing section 112, a linear actuator 260 is hingedly attached at its bottom end to the base 130. It is hingedly attached at its top end to the load arm 220. The actuator 260 includes an electric motor 262 for extending (lengthening) and retracting (shortening) the actuator. The motor 262 is controlled by a user interface comprising "up" and a "down" buttons 265, 266 on the tower 210. Pressing the "up" button 265 causes the actuator 260 to extend and pivot the vertical lift loading contact surfaces 250 upward and the sitting section's loading contact surfaces 230, 240 downward. Pressing the "down" button 266 causes the actuator 260 to retract, to pivot the vertical lift loading contact surfaces 250 downward and the sitting section's loading contact surfaces 230, 240 upward. The actuator 260 includes a second force sensor 274. This sensor 274, like the first force sensor 174, includes a load cell that outputs an analog signal related to force on the actuator shaft, electronic circuitry that converts the analog signal to a USB-compatible digital signal, and a USB port for outputting the digital signal.

The tower 210 supports the three video screen displays 121, 122, 123: The first display 121 faces axially toward the eyes of the user when the user sits on the chair structure 140 performing the sitting exercises. The second display 122 faces axially toward the eyes of the user when the user stands on the second platform 200 performing the vertical lift exercise. The first and second displays 121, 122 are axially spaced from each other and face axially away from each other. They are located axially between the sitting loading contact surfaces 241, 230, 240 and the vertical lift loading contact surfaces 250. They are indirectly secured, through the tower 210, to the base 130 and to each other.

The third display 123 faces transversely toward the eyes of the operator when the operator stands beside the machine 101 and faces the tower 210. This orientation of the third display 123 enables the third display 123 to display information to the operator that will not be visible by the user when the user performs the sitting or standing exercises. This orientation also enables the operator to glance at the third display's information while viewing the user from a side/front viewpoint of the user, both during the sitting and during the standing exercises, which is the optimum viewpoint for checking that the user's body is positioned properly for the exercises. The third screen 123 displays instructions to the operator on how guide to the user to properly perform each exercise. The third screen 123 also displays real time information regarding progress of each exercise, which enables the operator to advise the user as the exercise progresses, such as to encourage the user to maintain the applied force if the operator sees on the third display 123 that the applied force is dropping.

The tower 210 further supports an input device 280, in this example a keyboard, that is below the third display 123 and faces transversely toward the operator when the operator stands in front of the third display 123.

A processor 284 is located behind, and in the same housing as, the third display 123. The processor 284 is interfaced to the keyboard 280, the three displays 121, 122, 123, the force sensors 174, 274 and the actuator 260. It is also connected to the Internet via the appropriate international standard jacks 285. Power to these components is controlled by an on/off switch 286. The processor 284 reads force values from the first force sensor 174 through a USB cable to monitor the force applied by the user in the sitting exercises. The processor 284 also reads force values from the second force sensor 274 through another USB cable to monitor the force applied by the user in the vertical lift exercise.

The processor 284 also controls the amount of extension of the actuator 260. It also senses the actuator's length in terms of any appropriate parameter and units that are indicative of the actuator's amount of extension and thus indicative of the positions of the loading contact surfaces 230, 240, 250. This sensing is done by the processor 284 automatically, in that it does not require human intervention. For this purpose, the processor 284 can be electronically interfaced, for example, to the actuator's motor or controller, or to a displacement sensor that measures the actuator's length.

The sensing of the actuator's extension by the processor 284 can be done when the operator adjusts the length of the actuator 260 using the "up" and "down" buttons 265, 266 to adjust the height of the loading contact surfaces 230, 240, 250 to be appropriate for the current user for each of the three loading contact surface-related exercises. In subsequent sessions, the operator does not have to adjust the loading contact surfaces' height, because the processor 284 automatically controls the actuator 260 before each of the three loading contact surface-related exercises to return the respective loading contact surface 230, 240, 250 to the height it was, for the current user and current exercise, in the previous session. Therefore, when the user sits down to perform, for example, the chest press exercise, he/she will find the chest press loading contact surface 230 in the same position that it was when the user gripped it in the previous session. That renders the chest press result of the current session meaningfully comparable to the chest press results of previous sessions. Therefore, a graph of chest press results verses successive sessions will yield a meaningful indication of the user's progress for the chest press exercise. For the same reason, the three seat position settings used in the three respective sitting exercises in the first session are maintained in each subsequent session.

The 284 processor further enables the operator to enter, using the keyboard 280 and the third display 123, the seat position setting for the current user in the current leg press exercise, and displays that setting to the operator in the following session so that the operator can manually move the chair structure 140 to the same position setting for the leg press exercise in the following session.

The processor 284 is configured to output, through the Internet to a remote server (central data processing system), all data it has collected regarding the user, including data that was manually entered through the keyboard 280 or collected automatically from the force sensors 174, 274 and the actuator 260. The processor 284 does not store any of this information in its own local memory. In the following session, the processor 284 will download all the information for the current user from the remote server.

This thin client arrangement helps ensure confidentiality of the user's personal information, so that someone with access to the exercise machine 101 after the session will not be able to access a previous user's personal information.

This client arrangement also enables these exercise machines 101 to be located at different geographic locations around the world and provide the user the same experience independent of the location and the machine used. For example, there can be first and second substantially identical machines at two different geographic locations. The user can use the first machine for his/her first session, and can use the second machine for his/her second session. At the second session, the user's previously collected information will be available from the remote server at the second machine in the second session in the same way the information would have been available from the remote server at the first machine had the user used the first machine for the second session. Accordingly, the operator at the second machine in the second session will not have to re-enter data that a previous operator had already entered in a previous session. The user using the second machine in the second session will be presented with the loading contact surfaces 230, 240, 250 at their same positions and the seat 141 at its same position as in the first session. And the threshold forces that are calculated and then displayed to the user to meet and exceed for each exercise will be the same independent of what machine the user uses.

During each of the four exercises, the processor displays to the user a screen that is particular for that user and that exercise. The screen is displayed from the first display 121 during each of the sitting exercises and from the second display 122 during the standing exercise. An example of a chest press screen 300, displayed by the first display 121 during the leg press exercise, is shown in FIG. 10. Although this screen 300 is for the chest press, the screens for the other three exercises are similar.

The chest press screen 300 in FIG. 10 displays the following fields: A user name field 302 includes user's actual name or account name. An exercise filed 304 names the exercises being performed. An equipment settings field 306 includes an equipment setting, such as the seat position setting for the respective sitting exercise, that is either entered by the operator in the user's first session or downloaded from the remote server in a subsequent session.

A minimum hold time period 310 is the required minimum time duration the user must hold the applied force above the threshold force. This is preferably in the range 5-40 seconds, and preferably 5 seconds. It can, for example, start at 5 seconds and be incrementally increased with each successive session. A count-down timer 312 indicates the amount of the minimum hold time remaining that the user must maintain the force above the threshold force value. The count-down starts with the threshold period, which can be 5 seconds. The user is instructed to apply, to the leg press plate 214 or relevant loading contact surface 230, 240, 250, a consistently increasingly higher force until muscle failure. The count-down timer starts counting down when the applied force exceeds the threshold force. As the timer counts down, the user must maintain the applied force above threshold force, until the timer 312 reaches zero. When applying force, the user applies a force that is sufficient to achieve muscle failure, but not so much force that the muscle failure would occur before the timer reaches zero.

The screen 300 includes a virtual dial gauge 320 calibrated in lbs. A previous average force is displayed both textually in a previous average force field 322 and graphically as the upper limit 324 of a white band 326 on the dial gauge 320. This is the average force applied by the current user in the chest press exercise in the previous session. A tentative threshold average force is graphically displayed as a lower limit 330 of the white band 326 on the dial gauge 320. This threshold force 330 is calculated by the remote server based on the average chest press force of the previous session, such as a force about 15-25% lower than the previous session's average leg press force. An override force threshold 340 is a value entered by the operator on the keyboard 280 that overrides the tentative threshold force determined by the server. This override is called for, for example, if the user has an injury that would warrant adjusting the threshold force to a lower value. The currently-applied average force is displayed in real time both textually in a currently-applied average force field 350 and graphically as a needle 352 on the virtual gauge 320. This is the force applied by the user against the chest press loading contact surfaces 230 averaged over a required minimum time duration starting from when the currently applied force first exceeded the threshold force until either the present time or the end of the minimum hold time period, whichever is later. The user is instructed by the operator to try his/her best, during the exercise, to bring the needle past the previous average threshold force 306. When the timer 312 reaches zero, the virtual gauge turns red to indicate the exercise is over and the user may stop applying force.

A calibration force 361 is a value input by the processor 284 from the first force sensor 174, which is indicative of the sum of the weights of the user and the seat structure. A current net force 362 is the force sensed by the first force sensor 174, updated on the screen in real time; "net" meaning after subtracting the calibration force value that was measured before the exercise. A first force sensor reading 363 is the actual number the first force sensor 174 is outputting to the processor 284, updated on the screen in real time, and is displayed for troubleshooting purposes.

A virtual retry button 371 is pressed by the operator to repeat the current exercise. Although each exercise is normally performed only once, an exercise is repeated when the user's body was incorrectly positioned during the first try. A virtual next exercise button 372 is pressed to proceed to the next exercise. This button is pressed normally after the current exercise is completed, but can be pressed without performing the current exercise also.

While the chest press screen 300 of FIG. 10 is displayed by the first display 121 to the user, another chest press screen is displayed by the third display 123 to the operator. It includes all of the component of the first display's screen and additional information relating to the user and/or the exercise. This additional information is not visible to the user due to the third display's orientation relative to the user.

Method of Using the Exercise Machine

An exercise session can entail a procedure for using the machine 101 that includes the steps of login, weight calibration, chest press exercise, leg press exercise, core pull exercise, pull down exercise, and results print out. During the session, the user applies force for the minimum hold time only once for each exercise. The user does repeat the exercises until the next session. The next session is at the end of a recovery period, of for example typically two weeks, during which the user's muscles recover. Each exercise is a resistance isometric (fully contracted) exercise in which no component of the machine 1 moves while force is applied, including those components that are pivoted.

Login Step: A login screen appears on the third screen 123. It includes the user's session history. In the user's first session, the operator uses the login screen 123 and the keyboard 280 to enter the user's personal data, including name, ID, telephone number, address, age, date of birth, height and medical data such as prescription drugs taken and daily physical activity level. In each subsequent session, the operator uses to login screen and keyboard 280 to update or correct the personal data and record data regarding exercises performed in that session.

Calibrating Step: The chair structure 140 is slid to a predetermined calibration position setting and locked in place with the lock/release lever 158. The seat-supported foot rest 180 is rotated forward into its functional position. The user sits on the seat 141, with both feet resting on the seat-suspended foot rest 180 and the user's hands resting on his/her lap, so that the user's entire weight is supported by the chair structure 140. While the user remains in this position, the operator clicks a "calibrate" icon on a calibration screen displayed by the third display 123 which tares the force reading on the display to zero for the sitting exercises.

Chest Press: The chest press is a pushing exercise using of the arm muscles, which are the deltoid, triceps, and pectoral muscles. The load arm 220 is rotated to bring the chest press loading contact surfaces 230 one inch below the user's shoulder joint. This is performed by the motor of the actuator 260. During the user's first session, this is controlled by the operator using the "up" and "down" buttons as described above. However, in subsequent sessions, this is done automatically under control of the processor 284. The operator instructs the user to rest his/her feet on the seat-supported foot rest 180 and to place his/her hands on chest press loading contact surfaces 230 and bring elbows up to parallel, such that the hands, elbows, and shoulders are on a horizontal plane. If this is the user's first exercise session, the operator slides the seat chair structure 140 to a position in which the user's elbows are bent at an angle between 100° and 135°, locks the seat in place, and records this seat position setting into the processor 284 using the keyboard 280. In the user's subsequent sessions, the operator slides the seat to the position setting that is noted on the third display's screen 123, which is the position that the operator entered in a previous session.

The operator instructs the user to push his/her arms outward against the chest press loading contact surfaces 230 to their muscle failure point and hold the exercise for the entire minimum hold time. The average force exerted against the chest press loading contact surface 230 is displayed in real time by the needle 350 on the virtual gauge 320 shown on the first and third displays 121, 123. The count-down timer 312 starts counting down when the applied force exceeds the threshold force. The user forces the chest press loading contact surface 230 forward while continuously observing the needle 350 to ensure that the needle 350 remains above threshold force at least during the entire predetermined time period.

Leg Press: The leg press is a pushing exercise involving the leg muscles, which are the calves, quadriceps, and gluteus complex. The operator instructs the user to place his/her feet on the let press plate 214 and to grip the seat-side loading contact surfaces 190 to avoid sliding on the seat 141. In a first session, the operator slides the seat 141 to a position that causes the knees to bend with an angle of 90°-145°, and records the seat position setting using the third display 123 and the keyboard 280. In subsequent sessions, the operator will slide the seat 140 to a seat position setting that is displayed on the third display 123 which was recorded in a previous session. Under the operator's instruction, the user applies pressure through his/her heels, while keeping his/her entire back against the backrest 142 while pushing with his/her legs in an outward motion, and pushes to their muscle failure point and holds exercise for the entire minimum hold time period.

Core Pull: Core pull is a pulling exercise involving the biceps and lats (as stabilizers) and deep abdominals and hip flexors. The operator slides the seat 141 to proper position, and instructs the user to strap the seat belt 146 on tightly. With the seat-supported foot support 180 retracted, the user lets his/her feet hang and grasps the core pull loading contact surface 240 with palms facing towards the user. The operator instructs the user to pull the core pull loading contact surfaces 240 downward to reach muscle failure after the minimum hold time period.

Vertical Lift: Vertical lift is a pulling exercise involving the trapezius, spinal erectors, forearms, and hamstrings. The operator instructs the user to stand on the second platform, with feet about shoulder-width apart and thighs touching the second cross bar, and to look straight ahead at the second display. In a first session, the operator lowers the lift loading contact surface, using the "up" and "down" buttons, until it just reaches the first joint of the user's middle finger. The operator instructs the user to drop straight down and grab the loading contact surface with both hands, with feet directly underneath the loading contact surface. The operator instructs the user to use his/her back and leg muscles while arching the his/her back to lift the vertical lift loading contact surfaces 250 straight up and to pull to muscle failure point and hold exercise for the entire minimum hold time period.

After the final exercise of the current session, the computer outputs, via a printer, a printout 400 of the user's exercise history, as shown in FIG. 11. This printout 400 shows the account name 402. It further shows a percent increase 404 in applied force averaged over the four exercises. It further shows a regimen start date 406, printout date 407 that the report was called from the server, and the minimum hold time 408 of the current session.

The printout 400 further shows, for each the exercise, a bar graph 420 of an exercise result 421 vs. session number 422 or session date, for a chronological series of the sessions culminating with the current session. The result 421 in this example is average applied force in pounds, but can alternatively be length of time in seconds that the user maintained the force above the threshold, or a number of repetitions that the user maintained the force above the threshold force for the time threshold. The series of sessions for which the bar chart is displayed can include the current session and the fourteen previous sessions.

The printout 400 further includes an analysis and recommendations 422 in textual narrative format that is generated by the remote server via an array of algorithms that provide some comparative analysis of the present session against previous sessions, and also provides the user with instructions on when to return for the next exercise session. A legend 432 displays a color code that denotes how long the user took between sessions, which are useful to determining the proper recovery time.

At the end of the session, the operator uses the keyboard 280 and the third screen 123 to enter a command for the processor to upload, to the remote server via the computer's Internet connection, all data that was manually entered by the user and automatically acquired from the force sensors 174, 274 and the actuator 260 during the session. Then the processor 284 deletes all data regarding the user from its own local memory.

As schematically illustrated in FIG. 12, this exercise machine 101 can be one of a plurality of such machines 501 that are distributed around the world. Each machine 501 can be connected via the Internet 504 to an Application Service Provider (ASP) on the remote server 506. The Internet connection allows each machine 501 to support a thin client while the server 506 based software handles analysis, administration, and report development for both the user and all other authorized parties. The Internet 504 is ubiquitous and easily accessed. The Internet 504 also provides a standard for communications that allows simplification of support for and the upgrading of the individual the exercise machines 501 no matter where they are located worldwide. The ASP server 506, its security and availability is consistent with that used by banks and hospitals. The ASP server 506 can be mirrored by a server mirror 508 for further security. The ASP server 506 can also support other devices 510 that synergistically work within the server's parameters providing distributed thin client devices to connect to large servers that receive encrypted data, and then perform analyses of these data and further process the data for users, patients, physicians, insurance carriers, and other regulatory bodies, or other authorized parties. The ASP server 506 and server side functionality provides a capability to collect other/related medical and health data 512 and information that will assist the processing of any users active data for disease and medical condition processing. The ASP server side function also allows any and all machines 501 on the system to be updated 514 from the server 506, thus eliminating any human intervention at the user application level. The ASP 506 manages the authorization of access 516 to specific data files subject to full compliance with applicable law, UP protection and the appropriate security commitments from outside interests such as management of specific clients, Physicians, Insurance Carriers, Regulatory Agencies, and other UP authorized parties.

Although the detailed description contains many specifics, these should not be construed as limiting the scope of the present invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

No element, component or method step is intended to be dedicated to the public regardless of whether the element, component or method step is explicitly recited in the claims.

We claim:

1. A method of treating a disease or condition in a subject in need of treatment, the method comprising:
   (A) developing one or more exercise constraints as a function of the medical health information of the subject, including a state of the disease or condition;
   (B) having the subject perform a plurality of fully contracted exercises using exercise equipment, thereby producing an exercise result, wherein said exercise equipment has one or more strain gauges in order to impose or monitor exercise constraints in the one or more exercise constraints;
   (C) imposing a mandatory recovery period for said subject after step (B) during which time said subject does not perform the plurality of fully contracted exercises; and
   (D) having the subject repeat steps (B) and (C) using a new set of one or more exercise constraints that were refined based upon the exercise result of a previous instance of step (B), thereby treating the disease.

2. The method of claim 1, wherein the disease or condition is metabolic syndrome.

3. The method of claim 1, wherein the disease or condition is a deconditioned state.

4. The method of claim 1, wherein the disease or condition is osteoporosis or osteopenia.

5. The method of claim 1, wherein the disease or condition is a condition, and wherein the condition is susceptibility to injury.

6. The method of claim 1, wherein the disease or condition is diabetes.

7. The method of claim 1, wherein the disease or condition is a condition, wherein the condition is pain.

8. The method of claim 1, wherein the disease or condition is non-specific chronic lower back pain.

9. The method of claim 1, wherein the disease or condition is fibromyaligia.

10. The method of claim 1, wherein the disease or condition is a condition, wherein the condition is obesity.

11. The method of claim 1, wherein the disease or condition is Parkinson's disease or Multiple Sclerosis.

12. The method of claim 1, wherein the disease or condition is a condition, wherein the condition is lower back pain.

13. The method of claim 1, wherein the disease or condition is a condition, wherein the condition is a sports injury.

14. The method of claim 1, wherein the disease or condition is a brain disorder.

15. The method of claim 1, wherein an exercise constraint in said one or more exercise constraints is an amount of force that can be used in a fully contracted exercise in said plurality of fully contracted exercises.

16. The method of claim 1, wherein an exercise constraint in said one or more exercise constraints is a maximum amount of repetitions of a fully contracted exercise in said plurality of fully contracted exercises.

17. The method of claim 1, wherein said mandatory recovery time is a function of the exercise result.

18. The method of claim 1, wherein the exercise result is a length of time that the subject was able to exert a force during a fully contracted exercise in the plurality of fully contracted exercises.

19. The method of claim 17, wherein the exercise result is an amount of force that the subject was able to exert during a fully contracted exercise in the plurality of fully contracted exercises.

20. The method of claim 1, wherein the fully contracted exercise regimen works a plurality of muscle groups of the subject thereby accomplishing a full body stimulation resulting from the subject's force production.

21. The method of claim 1, wherein a fully contracted exercise in the plurality of fully contracted exercises stresses a muscle group to a point of failure.

22. The method of claim 1, wherein a length of time of the mandatory recovery period is a function of the exercise result and an experience trend measured among other subjects that use the fully contracted exercise regimen, wherein the other subjects have one or more characteristics in common with the subject.

23. The method of claim 1, the method further comprising: sending accounting and billing information relating to the fully contracted exercise regimen for said subject to a central data store and to also electronically interact with a physician of the subject, an employer of the subject, or an insurance carrier of the subject.

24. The method of claim 1, wherein the plurality of fully contracted exercises comprises one or more bench presses, one or more leg presses, one or more core pulls, and one or more vertical lifts.

25. The method of claim 1, wherein the subject is in a fully contracted position during an entirety of a fully contracted exercise in the plurality of fully contracted exercises.

26. The method of claim 1, wherein an exercise constraint in the one or more exercise constraints is a maximum amount of force of a fully contracted exercise in the plurality of fully contracted exercises.

* * * * *